US008119159B2

(12) United States Patent
Cumming et al.

(10) Patent No.: US 8,119,159 B2
(45) Date of Patent: *Feb. 21, 2012

(54) SOLID ORAL DOSAGE FORM CONTAINING AN ENHANCER

(75) Inventors: Kenneth Iain Cumming, Phibsboro (IE); Zebunissa Ramtoola, Dublin (IE); Thomas Waymond Leonard, Wilmington, NC (US)

(73) Assignee: Merrion Research III Limited, Dublin (IE)

( * ) Notice: Subject to any disclaimer, the term of this patent is extended or adjusted under 35 U.S.C. 154(b) by 707 days.

This patent is subject to a terminal disclaimer.

(21) Appl. No.: 11/400,689

(22) Filed: Apr. 7, 2006
(Under 37 CFR 1.47)

(65) Prior Publication Data

US 2007/0196464 A1    Aug. 23, 2007

Related U.S. Application Data

(63) Continuation-in-part of application No. 09/510,560, filed on Feb. 22, 2000, now abandoned.

(60) Provisional application No. 60/121,048, filed on Feb. 22, 1999.

(51) Int. Cl.
*A61K 9/20* (2006.01)

(52) U.S. Cl. ......... 424/465; 424/464; 424/451; 424/469

(58) Field of Classification Search ........................ None
See application file for complete search history.

(56) References Cited

U.S. PATENT DOCUMENTS

| | | | |
|---|---|---|---|
| 4,525,339 A | 6/1985 | Behl et al. | |
| 4,590,062 A | 5/1986 | Jang | |
| 4,654,155 A | 3/1987 | Kipp et al. | |
| 4,656,161 A | 4/1987 | Herr | |
| 4,764,375 A | 8/1988 | Paradissis | |
| 4,789,547 A | 12/1988 | Song et al. | |
| 4,996,058 A | 2/1991 | Sinnreich | |
| 5,110,606 A | 5/1992 | Geyer et al. | |
| 5,169,933 A * | 12/1992 | Anderson et al. | 530/391.3 |
| 5,190,748 A * | 3/1993 | Bachynsky et al. | 424/78.08 |
| 5,221,734 A | 6/1993 | Burk et al. | |
| 5,229,130 A | 7/1993 | Sharma et al. | |
| 5,288,497 A | 2/1994 | Stanley et al. | |
| 5,346,701 A * | 9/1994 | Heiber et al. | 424/435 |
| 5,444,041 A | 8/1995 | Owen et al. | |
| 5,506,207 A | 4/1996 | Rivier et al. | |
| 5,541,155 A | 7/1996 | Leone-Bay et al. | |
| 5,631,347 A | 5/1997 | Baker et al. | |
| 5,633,226 A | 5/1997 | Owen et al. | |
| 5,639,469 A | 6/1997 | Benes et al. | |
| 5,646,109 A | 7/1997 | Owen et al. | |
| 5,650,386 A | 7/1997 | Leone-Bay et al. | |
| 5,688,761 A | 11/1997 | Owen et al. | |
| 5,707,648 A | 1/1998 | Yiv | |
| 5,714,477 A | 2/1998 | Einarsson | |
| 5,736,161 A * | 4/1998 | Garces et al. | 424/493 |
| 5,821,222 A | 10/1998 | Bonse et al. | |
| 5,821,230 A | 10/1998 | Jiang et al. | |
| 5,840,685 A | 11/1998 | Fujii et al. | |
| 5,854,281 A | 12/1998 | Uekama et al. | |
| 5,863,555 A | 1/1999 | Heiber et al. | |
| 5,912,009 A | 6/1999 | Venkateshwaran et al. | |
| 5,952,000 A | 9/1999 | Venkateshwaran et al. | |
| 5,977,175 A | 11/1999 | Lin et al. | |
| 5,998,432 A | 12/1999 | Walsh et al. | |
| 6,001,390 A | 12/1999 | Yum et al. | |
| 6,004,984 A | 12/1999 | Goulet et al. | |
| 6,017,559 A | 1/2000 | Mulqueen et al. | |
| 6,017,944 A | 1/2000 | Chu et al. | |
| 6,025,366 A | 2/2000 | Walsh et al. | |
| 6,068,850 A | 5/2000 | Stevenson et al. | |
| 6,077,847 A | 6/2000 | Walsh et al. | |
| 6,077,858 A | 6/2000 | Goulet et al. | |
| 6,124,261 A | 9/2000 | Stevenson et al. | |
| 6,147,088 A | 11/2000 | Goulet et al. | |
| 6,150,352 A | 11/2000 | Goulet et al. | |
| 6,150,522 A | 11/2000 | Goulet et al. | |
| 6,156,767 A | 12/2000 | Goulet et al. | |
| 6,156,772 A | 12/2000 | Goulet et al. | |
| 6,200,602 B1 | 3/2001 | Watts et al. | |
| 6,214,798 B1 | 4/2001 | Semple et al. | |
| 6,235,712 B1 | 5/2001 | Stevenson et al. | |
| 6,270,804 B1 | 8/2001 | Getz et al. | |

(Continued)

FOREIGN PATENT DOCUMENTS

EP    0376534 A1    7/1990

(Continued)

OTHER PUBLICATIONS

Sawada et al., Pharmaceutical Research, 8(11):1365-1371 (1991).*
Anderberg, E.K. et al., Sodium Caprate Elicits Dilatiations in Human Intestinal Tight Junctions and Enhances Durg Absorption by the Paracellular Route, Pharmaceutical Research, vol. 10, No. 6, pp. 857-864, 1993.
Andriuoil, G. et al., Heparin by Alternative Routes of Administration, Haemostasis, vol. 20, Supplemental 1, pp. 154-158, 1990.
Artursson, P., Epithelial Transport of Drugs in Cell Culture: I: A Model for Studing the Passive Diffusion of Drugs over Intestinal Absorbative (Caco-2) Cells, Journal Pharmaceutical Studies, vol. 79, No. 7, pp. 476-482, 1990.

(Continued)

*Primary Examiner* — Jeffrey S. Lundgren
*Assistant Examiner* — Stephanie Springer
(74) *Attorney, Agent, or Firm* — Myers Bigel Sibley & Sajovec P.A.

(57) ABSTRACT

The invention relates to a pharmaceutical composition and oral dosage forms comprising a bisphosphonate in combination with an enhancer to promote absorption of the bisphosphonate at the GIT cell lining. The enhancer is a medium chain fatty acid or a medium chain fatty acid derivative having a carbon chain length of from 6 to 20 carbon atoms. Preferably, the solid oral dosage form is a controlled release dosage form such as a delayed release dosage form.

40 Claims, 16 Drawing Sheets

U.S. PATENT DOCUMENTS

| | | | |
|---|---|---|---|
| 6,326,360 | B1 | 12/2001 | Kanazawa et al. |
| 6,372,728 | B1 * | 4/2002 | Ungell .................. 514/109 |
| 6,379,960 | B1 | 4/2002 | Popoff et al. |
| 6,468,559 | B1 | 10/2002 | Chen et al. |
| 6,638,530 | B1 | 10/2003 | Ishibashi et al. |
| 6,747,014 | B2 * | 6/2004 | Teng et al. .................. 514/44 |
| 6,747,125 | B1 | 6/2004 | Hoeger et al. |
| 6,875,843 | B2 | 4/2005 | Jacobson |
| 6,949,258 | B2 | 9/2005 | Zhang |
| 7,098,305 | B2 | 8/2006 | Deghenghi et al. |
| 7,154,002 | B1 | 12/2006 | Bressi et al. |
| 7,214,662 | B2 | 5/2007 | Sarlikiotis et al. |
| 7,410,957 | B2 | 8/2008 | Bauss et al. |
| 7,658,938 | B2 | 2/2010 | Cumming et al. |
| 7,670,626 | B2 | 3/2010 | Clancy et al. |
| 7,704,977 | B2 | 4/2010 | Leonard |
| 2002/0002140 | A1 | 1/2002 | Holick et al. |
| 2003/0091623 | A1 | 5/2003 | Cumming et al. |
| 2003/0114525 | A1 | 6/2003 | Kammer et al. |
| 2003/0139378 | A1 | 7/2003 | Daifotis et al. |
| 2003/0176397 | A1 | 9/2003 | Lichtenberger |
| 2003/0181421 | A1 | 9/2003 | Horowitz et al. |
| 2004/0087631 | A1 | 5/2004 | Bacopoulos et al. |
| 2004/0147484 | A1 | 7/2004 | Boyd et al. |
| 2004/0157799 | A1 | 8/2004 | Seaman et al. |
| 2005/0080075 | A1 | 4/2005 | Nichols et al. |
| 2005/0157799 | A1 | 7/2005 | Raman |
| 2005/0221501 | A1 | 10/2005 | Arnot et al. |
| 2005/0232981 | A1 | 10/2005 | Ben-Sasson |
| 2006/0210639 | A1 | 9/2006 | Liversidge et al. |
| 2007/0021357 | A1 | 1/2007 | Tobia et al. |
| 2007/0021378 | A1 | 1/2007 | Varki et al. |
| 2007/0060509 | A1 | 3/2007 | Kanikanti et al. |
| 2007/0148228 | A1 | 6/2007 | Cumming et al. |
| 2007/0212395 | A1 | 9/2007 | Donello et al. |
| 2007/0219131 | A1 | 9/2007 | Ben-Sasson |
| 2007/0238707 | A1 | 10/2007 | Leonard |
| 2007/0292512 | A1 | 12/2007 | Leonard et al. |
| 2008/0171848 | A1 | 7/2008 | Christiansen et al. |
| 2008/0275001 | A1 | 11/2008 | Cumming et al. |
| 2009/0004281 | A1 | 1/2009 | Nghiem et al. |
| 2009/0060861 | A1 | 3/2009 | Poulsen |
| 2009/0274758 | A1 | 11/2009 | Pinhasi et al. |
| 2009/0280169 | A1 | 11/2009 | Leonard |
| 2009/0280170 | A1 | 11/2009 | Lee et al. |
| 2010/0105627 | A1 | 4/2010 | Salama et al. |

FOREIGN PATENT DOCUMENTS

| | | |
|---|---|---|
| EP | 0 497 162 | 8/1992 |
| EP | 0 517 211 | 12/1992 |
| EP | 0580074 A1 | 1/1994 |
| EP | 0747390 A2 | 12/1996 |
| EP | 0667148 B1 | 7/2002 |
| EP | 1246839 B1 | 6/2004 |
| EP | 1674082 A1 | 6/2006 |
| EP | 1339411 | 7/2007 |
| GB | 953626 | 3/1964 |
| IE | 63119 | 3/1995 |
| JP | 02180837 | 7/1990 |
| JP | 2282327 | 11/1990 |
| JP | 6040949 | 2/1994 |
| JP | 11035458 | 2/1999 |
| JP | 2004529953 | 9/2004 |
| WO | 8404674 | 12/1984 |
| WO | WO 93/05903 A1 | 4/1993 |
| WO | 9321907 | 11/1993 |
| WO | WO 93/21907 | 11/1993 |
| WO | WO 94/010983 A1 | 5/1994 |
| WO | 9522319 | 8/1995 |
| WO | 9534294 | 12/1995 |
| WO | 9705903 | 2/1997 |
| WO | WO 97/05903 * | 2/1997 |
| WO | 9901579 | 1/1999 |
| WO | WO 99/01579 | 1/1999 |
| WO | WO 99/02120 A2 | 1/1999 |
| WO | WO 99/02485 A1 | 1/1999 |
| WO | WO 99/45934 A1 | 9/1999 |
| WO | WO 00/22909 A2 | 4/2000 |
| WO | WO 00/50012 | 8/2000 |
| WO | WO 00/61111 A1 | 10/2000 |
| WO | WO 01/89479 A2 | 11/2001 |
| WO | WO 02/092070 | 11/2002 |
| WO | WO 03/003999 A2 | 1/2003 |
| WO | WO 03-045419 A1 | 6/2003 |
| WO | WO 03/047493 A2 | 6/2003 |
| WO | WO 2005/055973 A2 | 6/2005 |
| WO | WO 2005/063218 | 7/2005 |
| WO | WO 2006-010155 A2 | 1/2006 |

OTHER PUBLICATIONS

Aungst, B. J. et al., "Enhancement of the Intestinal Absorption of Peptides and Non-peptides", Journal of Controlled Release, vol. 41, No. 1, pp. 19-31, Aug. 1, 1996.

Brayden, D. et al., "Heparin Absorption Across the Intestine: Effects of Sodium N-[8-(2-Hydroxybenzoyl)Amino]Caprylate in Rat In Situ Intestinal Instillations and in Caco-2 Monolayers", Pharmaceutical Research, vol. 14, No. 12, pp. 1772-1779, 1997.

Cumming, K.I. and Winfield, A.J., "In Vitro Evaluation of a Series of Sodium Carboxylates as Dermal Penetration Enhancers", Int J. Pharm., vol. 108, pp. 141-148, 1994.

Doluisio, J. T., et al., Drug Absorption I: An In Situ Rat Gut Technique Yielding Realistic Absorption Rates, Journal Pharmaceutical Studies, vol. 58, No. 10, pp. 1196-1200, 1969.

Lindmark, T. et al., Machanisms of Absorption Enhancement by Medium Chain Fatty Acids in Intestinal Epithelial Caco-2 Cell Monolayers[1], Journal of Pharmacology and Experimental Therapeutics, vol. 275, No. 2, pp. 958-964, 1995.

Lindmark, T. et al., "Mechanism of Absorption Enhancement in Humans After Rectal Administration of Ampilillin in Suppositories Containing Sodium Caprate", Pharmaceutical Research, vol. 14, No. 7, pp. 930-935, 1997.

Murakami, M. et al., "Effect of Oleic Acid Vesicles on Intestinal Absorption of Carboxyfluorescein in Rats", Pharmaceutical Research, vol. 3, No. 1, pp. 35-40, 1986.

Muranushi, N. et al., "The Effects of Fatty Acids and Their Derivatives on the Intestinal Absorption of Insulin in Rats", Drug Development and Industrial Pharmacy, vol. 19, No. 8, pp. 929-941, 1993.

Oda, et al., Absorption Enhancement of Argatroban by Medium Chain Fatty Acid Sodium Salts, Proceedings Int'l Symp. Control. Rel. Bioact Mater, 24, pp. 283-284, 1997.

Palin, K. J., et al., "The Oral Aborption of Cefoxitin from Oil and Emulsion Vehicles in Rats", International Journal of Pharmaceutics, vol. 33, pp. 99-104, 1986.

Sawada, T., et al., Role of Paracellular Pathway in Nonelectrolyte Permeation Across Rat Colon Epithelium Enhanced by Sodium Caprate and Sodium Caprylate, Pharmaceutical Research, vol. 8, No. 11, pp. 1365-1371, 1991.

Tomita, M. et al., Enhancement of Colonic Drug Absorption by the Paracellular Permeation Route, Pharmaceutical Research, vol. 5, No. 6, pp. 341-346, 1988.

Tomita, M. et al., Enhancement of Colonic Drug Absorption by the transcellular Permeation Route, Pharmaceutical Research, vol. 5, No. 12, pp. 786-789, 1988.

Tomita, M. et al., Differences in the Enhancing Effects of Sodium Caprate on Colonic and Jejunal Drug Absorption, Pharmaceutical Research, vol. 9, No. 5, pp. 648-653, 1992.

Tomita, M. et al., Absorption-Enhancing Mechanism of Sodium Caprate and Decanoylcarnitine in Caco-2 Cells, The Journal of Pharmacology and Experimental Therapeutics, vol. 272, No. 2, pp. 739-743, 1995.

Yeh., P. et al., Effect of Medium-chain Glycerides on Physiological Properties of Rabbit Intestinal Epithelium in Vitro, Pharmaceutical Research, vol. 11, No. 8, pp. 1148-1154, 1994.

Extended European Search Report dated Feb. 9, 2010; Application No. 07755266.9.

Aungst, "Structure/effect studies of fatty acid isomers as skin penetration enhancers and skin irritants," Pharm. Res. 6:244-247 (1989).

Bennett et al., "Pulmonary Delivery of Detirelex by Intratracheal Instillation and Aerosol Inhalation in the Briefly Anesthetized Dog," Pharm. Res. 11:1048-1054 (1994).

Declaration of Dr. Thomas W. Leonard from European Patent Application EP 00905186.3.
Gennaro, "Remington: The Science and Practice of Pharmacy," 19th Edition, Mack Publishing Co., p. 1618 (1995).
Lambent Technologies, "Technical Data Sheet for Lumulse L-4, Lumulse L-12, and Lumulse L-23", pp. 1-2 (2004).
Lambent Technologies, webpage publication at www.petrofer.com/prodinfo.asp?bus=2&mkt=4&app=3.
Muranishi, "Absorption Enhancers," Crit. Rev. Ther. Drug Carrier Systems 7:1-33 (1990).
Schneider et al., "Evaluation of drug penetration into human skin ex vivo using branched fatty acids and propylene glycol," Int. J. Pharm. 145:187-196 (1996).
WPI Database, Accession No. 1984-142694, English language abstract of JP 59073600.
WPI Database, Accession No. 1992-028863, English language abstract of JP 03275633.
WPI Database, Accession No. 1997-287727, English language abstract of RU 2068689.
U.S. Appl. No. 11/733,007, filed Apr. 9, 2007; Office Action mailed Jan. 29, 2009.
U.S. Appl. No. 09/510,560, filed Feb. 22, 2000; Office Action mailed Mar. 26, 2001.
U.S. Appl. No. 09/510,560, filed Feb. 22, 2000; Office Action mailed Jul. 15, 2002.
U.S. Appl. No. 09/510,560, filed Feb. 22, 2000; Office Action mailed Oct. 22, 2003.
U.S. Appl. No. 09/510,560, filed Feb. 22, 2000; Office Action mailed Jun. 4, 2004.
U.S. Appl. No. 09/510,560, filed Feb. 22, 2000; Office Action mailed May 18, 2005.
U.S. Appl. No. 09/510,560, filed Feb. 22, 2000; Office Action mailed Nov. 21, 2005.
U.S. Appl. No. 09/510,560, filed Feb. 22, 2000; Office Action mailed Jun. 14, 2006.
U.S. Appl. No. 09/510,560, filed Feb. 22, 2000; Office Action mailed Dec. 15, 2006.
U.S. Appl. No. 09/510,560, filed Feb. 22, 2000; Office Action mailed Aug. 23, 2007.
U.S. Appl. No. 09/510,560, filed Feb. 22, 2000; Office Action mailed Feb. 20, 2008.
U.S. Appl. No. 09/510,560, filed Feb. 22, 2000; Office Action mailed Sep. 17, 2008.
Chan et al., "Depsipeptide (FR901228, NSC-630176) pharmacokinetics in the rat by LC/MS/MS," Invest. New Drugs 15:195-206 (1997).
Mishima et al., "Studies on the Promoting Effects of Medium Chain Fatty Acid Salts on the Nasal Absorption of Insulin in Rats," J. Pharmacobio-Dyn., 10:624-631 (1987).
Morishita et al., "Site-Dependent Effect of Aprotinin, Sodium Caprate, $Na_2EDTA$ and Sodium Glycocholate on Intestinal Absorption of Insulin," Biol. Pharm. Bull. 16:68-72 (1993).
Yamamoto et al., "Pulmonary absorption enhancement of peptides by absorption enhancers and protease inhibitors," J. Control. Release, 41:57-67 (1996).
Yang et al., Deposition of insulin powders for inhalation in vitro and pharmacodynamic evaluation of absorption promoters in rats, Acta Pharmaceutica Sinica 40:1069-1074 (2005).
Zhou et al., "Effects of cholic acid and other enhancers on the bioavailability of insulin from a subcutaneous site," Int. J. Pharm. 69:29-41 (1991).
U.S. Appl. No. 11/450,641, filed: Jun. 9, 2006; Office Action mailed Jun. 25, 2009.
Lambent Technologies, "Material Safety Data Sheet for Lumulse L-12", pp. 1-3 (2004).
U.S. Appl. No. 09/510,560, filed Feb. 22, 2000; Office Action mailed May 27, 2009.
U.S. Appl. No. 11/733,007, filed Apr. 9, 2007; Office Action mailed Aug. 17, 2009.
U.S. Appl. No. 11/761,233, filed Jun. 11, 2007; Office Action mailed Sep. 1, 2009.
U.S. Appl. No. 12/481,952, filed Jun. 10, 2009.
U.S. Appl. No. 12/553,196, filed Sep. 3, 2009.
U.S. Appl. No. 11/450,641; Filed: Jun. 9, 2006 ; Office Action mailed Nov. 9, 2011.
U.S. Appl. No. 12/172,707; Filed: Jul. 14, 2008; Office Action mailed Nov. 9, 2011.
Fernandez et al., "Comparative study on digestive lipase activities on the self emulsifying excipient Labrasol®, medium chain glycerides and PEG esters," Biochim. Biophys. Acta 1771:633-640 (2007).
Kajii et al., "Fluorescence study of the membrane-perturbing action of sodium caprylate as related to promotion of drug absorption," J. Pharm. Sci. 77:390-392 (1988).
Lesnyak, "Medicamental methods of treating osteoporosis," Gynecology, vol. 7 (2005); accessed at www.consiliurn-medicum.com/article/7685.
U.S. Appl. No. 12/172,707; filed: Jul. 14, 2008; office action mailed Apr. 27, 2011.
U.S. Appl. No. 12/553,196; filed: Sep. 3, 2009; office action mailed Mar. 31, 2011.
U.S. Appl. No. 12/436,990; filed: May 7, 2009; office action mailed Mar. 16, 2011.
Canadian Application No. 2,363,123, filed Feb. 22, 2000; office action mailed May 18, 2010.
U.S. Appl. No. 13/073,202, filed Mar. 28, 2011.
U.S. Appl. No. 13/014,156, filed Jan. 26, 2011.
Sikora, "Cancer drug development in the post-genomic age," Curr. Sol. 81:549-54 (2001).
Zips at al., "New anticancer agents: In vitro and in vivo evaluation," In vivo 19:108 (2005).
U.S. Appl. No. 12/481,952; Filed: Jun. 10, 2009; Office Action mailed Jul. 26, 2011.
U.S. Appl. No. 12/172,707; Filed: Jul. 14, 2008; Office Action mailed Jan. 4, 2011.
U.S. Appl. No. 12/553,196; Filed: Sep. 3, 2009; Office Action mailed Sep. 24, 2010.
U.S. Appl. No. 13/242,601, filed Sep. 23, 2011.
Choay et al., "Structure-activity relationship in heparin: A synthetic pentasaccharide with high affinity for antithrombin III and eliciting high anti-factor Xa activity," Biochem. Biophys. Res. Commun. 116:492-499 (1983).
U.S. Appl. No. 12/768,008; Filed Apr. 27, 2010; Office Action mailed Aug. 2, 2011.
Japanese Application No. 2000-600624, filed Feb. 22, 2000; office action mailed Jul. 5, 2011.
U.S. Appl. No. 12/436,990; Filed: May 7, 2009; Office Action mailed Oct. 7, 2011.
U.S. Appl. No. 12/436,990; Filed: May 7, 2009; Office Action mailed Sep. 14, 2010.
Allen, "Ansel's Pharmaceutical Dosage Forms and Drug Delivery Systems," 8th Ed., Lippincott Williams & Wilkins, 51-58 (2005).
Baker et al., "Role of Body Surface Area in Dosing of Investigatioanl Agents in Adults, 1991-2001," J. Natl. Cancer Inst. 94:1883-1888 (2002).
Hahn, "Chemotherapy Dose Calculation and Administration in Exotic Animal Species," Sem. Avian Exotic Pet Med. 14:193-198 (2005).
Massa et al., "3-(4-Aroyl-1H-pyrrol-2-yl)-N-hydroxy-2-propenamides, a New Class of Synthetic Histone Deacetylase Inhibitors," J. Med. Chem. 44:2069-2072 (2001).
Moradei et al., "Histone deacetylase inhibitors: Latest developments, trends and prospects," Curr. Med. Chem. 5(5):529-560 (2005).
Poster Presentation entitled "A Phase I Trial and Pharmacokinetic Study of Depsipeptide in Pediatric Patients with Refractory Solid Tumors: A Children's Oncology Group Study" at American Society of Clinical Oncology meeting, May 2005, abstract 8528 (Fouladi et al.).
Sawyer et al., "Body surface area as a determinant of pharmacokinetics and drug dosing," Invest. New Drugs 19:171-177 (2001).
Sinko, "Martin's Physical Pharmacy and Pharmaceutical Sciences," 5th Ed., Lippincott Williams & Wilkins, 355-357 (2006).
U.S. Appl. No. 11/450,641; Filed: Jun. 9, 2006; Office Action mailed Apr. 14, 2010.
U.S. Appl. No. 11/761,233; Filed: Jun. 11, 2007; Office Action mailed Jun. 28, 2010.
U.S. Appl. No. 12/768,008; Filed: Apr. 27, 2010.

U.S. Appl. No. 12/767,076; Filed: Apr. 26, 2010.

Allen, "Ansel's Pharmaceutical Dosage Forms and Drug Delivery Systems," 8th Ed., Lippincott Williams & Wilkins, 51-58 (2005).

Baker et al., "Role of Body Surface Area in Dosing of Investigatioanl Agents in Adults, 1991-2001," J. Natl. Cancer Inst. 94:1883-1888 (2002).

Grohganz et al., "Development and in vitro evaluation of a liposome based implant formulation for the decapeptide cetrorelix," Eur. J. Pharm. Biopharm. 59:439-448 (2004).

Hahn, "Chemotherapy Dose Calculation and Administration in Exotic Animal Species," Sem. Avian Exotic Pet Med. 14:193-198 (2005).

Hild et al., "The ability of a gonadotropin-releasing hormone antagonist, acyline, to prevent irreversible infertility induced by the indenopyridine, CDB-4022, in adult male rats: the role of testosterone," Biol. Reproduction 71:348-358 (2004).

Jiang et al., "GnRH antagonists: a new generation of long acting analogues incorporating *p*-ureidophenylalanines at positions 5 and 6," J. Med. Chem. 44:453-467 (2000).

Massa et al., "3-(4-Aroyl-1H-pyrrol-2-y1)-N-hydroxy-2-propenamides, a New Class of Synthetic Histone Deacetylase Inhibitors," J. Med. Chem. 44:2069-2072 (2001).

Mechanick et al., "Effect of a Convenient Single 90-mg Pamidronate Dose on Biochemical Markers of Bone Metabolism in Patients With Acute Spinal Cord Injury," J. Spinal Cord Med. 29(4):406-412 (2006).

Moradei et al., "Histone deacetylase inhibitors: Latest developments, trends and prospects," Curr. Med. Chem. 5(5):529-560 (2005).

Octreotide, Wikipedia. Printed Mar. 23, 2009. 3 pp.

Poster Presentation entitled "A Phase I Trial and Pharmacokinetic Study of Depsipeptide in Pediatric Patients with Refractory Solid Tumors: A Children's Oncology Group Study" at American Society of Clinical Oncology meeting, May 2005, abstract 8528 (Fouladi et al.).

Sawyer et al., "Body surface area as a determinant of pharmacokinetics and drug dosing," Invest. New Drugs 19:171-177 (2001).

Sinko, "Martin's Physical Pharmacy and Pharmaceutical Sciences," 5$^{th}$ Ed., Lippincott Williams & Wilkins, 355-357 (2006).

Somatostatin, Wikipedia. Printed Mar. 23, 2009. 4 pp.

U.S. Appl. No. 11/450,641; Filed: Jun. 9, 2006; Office Action mailed Apr. 14, 2010.

U.S. Appl. No. 11/761,233; Filed: Jun. 11, 2007; Office Action mailed Jun. 28, 2010.

U.S. Appl. No. 12/768,008; Filed: Apr. 27, 2010.

U.S. Appl. No. 12/767,076; Filed: Apr. 26, 2010.

U.S. Appl. No. 12/712,527; Filed: Feb. 25, 2010.

International Application No. PCT/GB00/000628, filed Feb. 22, 2000, international search report and written opinion.

Canadian Application No. 2,363,123, filed Feb. 22, 2000; office action mailed Jun. 30, 2008.

Canadian Application No. 2,363,123, filed Feb. 22, 2000; office action mailed Jun. 12, 2009.

European Application No. 00905186.3, filed Feb. 22, 2000; office action mailed Aug. 4, 2003.

European Application No. 00905186.3, filed Feb. 22, 2000; office action mailed Jul. 12, 2004.

European Application No. 00905186.3, filed Feb. 22, 2000; office action mailed Jun. 29, 2005.

Japanese Application No. 2000-600624, filed Feb. 22, 2000; office action mailed Apr. 6, 2010.

* cited by examiner

SOLID ORAL DOSAGE FORM CONTAINING AN ENHANCER

This application is a Continuation-in-part of application Ser. No. 09/510,560 filed Feb. 22, 2000 which claims the benefit of Provisional Application No. 60/121,048 filed Feb. 22, 1999.

FIELD OF THE INVENTION

The present invention relates to a compositions and solid oral dosage forms containing an enhancer. In particular the invention relates to compositions and solid oral dosage forms comprising a pharmaceutically active ingredient in combination with an enhancer which enhances the bioavailability and/or the absorption of the active ingredient.

BACKGROUND OF THE INVENTION

The epithelial cells lining the lumenal side of the gastrointestinal tract (GIT) can be a major barrier to drug delivery via oral administration. However, there are four recognized transport pathways which can be exploited to facilitate drug delivery and transport: the transcellular, paracellular, carrier-mediated and transcytotic transport pathways. The ability of a drug, such as a conventional drug, a peptide, a protein, a macromolecule or a nano- or microparticulate system, to "interact" with one or more of these transport pathways may result in increased delivery of that drug from the GIT to the underlying circulation.

Certain drugs utilize transport systems for nutrients which are located in the apical cell membranes (carrier mediated route). Macromolecules may also be transported across the cells in endocytosed vesicles (transcytosis route). However, many drugs are transported across the intestinal epithelium by passive diffusion either through cells (transcellular route) or between cells (paracellular). Most orally administered drugs are absorbed by passive transport. Drugs which are lipophilic permeate the epithelium by the transcellular route whereas drugs that are hydrophilic are restricted to the paracellular route.

Paracellular pathways occupy less than 0.1% of the total surface area of the intestinal epithelium. Further, tight junctions, which form a continuous belt around the apical part of the cells, restrict permeation between the cells by creating a seal between adjacent cells. Thus, oral absorption of hydrophilic drugs such as peptides can be severely restricted. Other barriers to absorption of drugs may include hydrolyzing enzymes in the lumen brush border or in the intestinal epithelial cells, the existence of the aqueous boundary layer on the surface of the epithelial membrane which may provide an additional diffusion barrier, the mucus layer associated with the aqueous boundary layer and the acid microclimate which creates a proton gradient across the apical membrane. Absorption, and ultimately bioavailability, of a drug may also be reduced by other processes such as P-glycoprotein regulated transport of the drug back into the gut lumen and cytochrome P450 metabolism. The presence of food and/or beverages can also interfere with absorption and bioavailability.

Bisphosphonates are a family of drugs used to prevent and treat bone fractures, osteoporosis, Paget's disease, metastatic bone cancer, and other bone diseases with high bone resorption. Bisphosphonates bind to bone hydroxyapatite and slow down bone-eroding cells known as osteoclasts. This effect allows the bone-building cells known as osteoblasts to work more effectively.

Some of the limitations with conventional bisphosphonates include irritation of the upper GIT, such as esophageal ulcers, and low bioavailability. As a result, conventional bisphosphonates require a specific dosing regimen so that the patient can absorb some of the drug properly and avoid side effects. Because many foods, beverages, medications and calcium interfere with absorption, conventional bisphosphonates must be administered on an empty stomach and, depending on the particular bisphosphonate, must wait from 30 minutes to two hours before consuming any food, beverages (other than water), medications or calcium supplements. As esophageal ulcers are a known side effect, dosing regimens for conventional bisphosphonates specify that patients consume an entire glass of water with the dosage form and avoid assuming a horizontal orientation, such as by lying down, within 30 to 60 minutes after administration.

The specific characteristics of alendronate served to exemplify the members of the class of bisphosphonates and the issues associated with them. Alendronate is a white, crystalline, odourless, non-hygroscopic bisphosphonate prepared by chemical synthesis. Alendronate monosodium trihydrate has a molecular weight of 325.1. Alendronate is approved in the U.S. for the prevention and treatment of osteoporosis in men and postmenopausal women, and for the treatment of Paget's disease of bone and glucocorticoid induced osteoporosis in both sexes. Like other bisphosphonates, alendronate binds to bone hydroxyapatite and specifically inhibits the activity of osteoclasts. Alendronate reduces bone turnover in human and animal models and decreases activation frequency, reducing bone resorption in both cortical and trabecular bone and ultimately increasing bone density and strength.

The oral bioavailability of alendronate is very low and independent of the dose (5-80 mg), averaging 0.76% in women and 0.59% in men. Presystemic metabolism does not occur. Following oral administration of conventional forms of alendronate, 40% of the dose absorbed is excreted in the urine within 8 hours and a further 5% is excreted over the next 64 hours. Sixty to seventy per cent of the absorption occurs within 1 hour of dosing. Bioavailability is markedly reduced by coincident consumption of food (85%-90%) and even consumption of coffee or orange juice will impair absorption by as much as 60% or more. Coincident medication will also reduce absorption, as any calcium-containing compounds and multivalent cations will bind to the bisphosphonate. Elevation of gastric pH above 6 is associated with a twofold increase in alendronate absorption. Alendronate is not metabolized and is excreted unchanged with renal clearance comparable to the glomerular filtration rate.

Bisphosphonate compositions and oral dosage forms with improved systemic bioavailability which are not subject to the dosing restrictions of conventional bisphosphonates would represent a considerable benefit for patients. As a result, new strategies for delivering drugs across the GIT cell layers are needed, particularly for bisphosphonates.

Numerous potential absorption enhancers have been identified. For instance, medium chain glycerides have demonstrated the ability to enhance the absorption of hydrophilic drugs across the intestinal mucosa (Pharm. Res. (1994), 11, 1148-54). However, the importance of chain length and/or composition is unclear and therefore their mechanism of action remains largely unknown. Sodium caprate has been reported to enhance intestinal and colonic drug absorption by the paracellular route (Pharm. Res. (1993) 10, 857-864; Pharm. Res. (1988), 5, 341-346). U.S. Pat. No. 4,656,161 (BASF AG) discloses a process for increasing the enteral absorbability of heparin and heparinoids by adding non-ionic surfactants such as those that can be prepared by reacting ethylene oxide with a fatty acid, a fatty alcohol, an alkylphenol or a sorbitan or glycerol fatty acid ester.

U.S. Pat. No. 5,229,130 (Cygnus Therapeutics Systems) discloses a composition which increases the permeability of skin to a transdermally administered pharmacologically active agent formulated with one or more vegetable oils as skin permeation enhancers. Dermal penetration is also known to be enhanced by a range of sodium carboxylates [Int. J. of Pharmaceutics (1994), 108, 141-148]. Additionally, the use of essential oils to enhance bioavailability is known (U.S. Pat. No. 5,665,386 AvMax Inc. and others). It is taught that the essential oils act to reduce either, or both, cytochrome P450 metabolism and P-glycoprotein regulated transport of the drug out of the blood stream back into the gut.

Often, however, the enhancement of drug absorption correlates with damage to the intestinal wall. Consequently, limitations to the widespread use of GIT enhancers are frequently determined by their potential toxicities and side effects. Additionally and especially with respect to peptide, protein or macromolecular drugs, the "interaction" of the GIT enhancer with one of the transport pathways should be transient or reversible, such as a transient interaction with or opening of tight junctions so as to enhance transport via the paracellular route.

As mentioned above, numerous potential enhancers are known. However, this has not led to a corresponding number of products incorporating enhancers. One such product currently approved for use in Sweden and Japan is the Doktacillin™ suppository [Lindmark et al. Pharmaceutical Research (1997), 14, 930-935]. The suppository comprises ampicillin and the medium chain fatty acid, sodium caprate (C10).

Provision of a solid oral dosage form which would facilitate the administration of a drug together with an enhancer is desirable. The advantages of solid oral dosage forms over other dosage forms include ease of manufacture, the ability to formulate different controlled release and extended release formulations and ease of administration. Administration of drugs in solution form does not readily facilitate control of the profile of drug concentration in the bloodstream. Solid oral dosage forms, on the other hand, are versatile and may be modified, for example, to maximize the extent and duration of drug release and to release a drug according to a therapeutically desirable release profile. There may also be advantages relating to convenience of administration increasing patient compliance and to cost of manufacture associated with solid oral dosage forms.

SUMMARY OF THE INVENTION

According to one aspect of the present invention, the compositions and dosage forms made therefrom of the present invention comprise a drug and an enhancer to promote absorption of the bisphosphonate at the GIT cell lining wherein the enhancer is a medium chain fatty acid or a medium chain fatty acid derivative having a carbon chain length of from 6 to 20 carbon atoms; with the provisos that (i) where the enhancer is an ester of a medium chain fatty acid, said chain length of from 6 to 20 carbon atoms relates to the chain length of the carboxylate moiety, and (ii) where the enhancer is an ether of a medium chain fatty acid, at least one alkoxy group has a carbon chain length of from 6 to 20 carbon atoms, and wherein the enhancer and the composition are solids at room temperature.

According to another aspect of the present invention, the compositions and dosage forms made therefrom comprise a drug and an enhancer to promote absorption of the bisphosphonate at the GIT cell lining, wherein the only enhancer present in the composition is a medium chain fatty acid or a medium chain fatty acid derivative having a carbon chain length of from 6 to 20 carbon atoms.

In embodiments in which the drug comprises a bisphosphonate, the drug may be selected from the group that includes alendronate, clodronate, etidronate, incadronate, ibandronate, minodronate, pamidronate, risedronate, tiludronate, zoledronate and derivatives thereof. The bisphosphonate dosage form may be an enteric coated instant release solid oral dosage form which provides improved oral bioavailability and minimizes the risk of local irritation of the upper GIT. In one embodiment, the bisphosphonate is zoledronic acid.

The dosage forms can be a tablet, a multiparticulate or a capsule. The multiparticulate can be in the form of a tablet or contained in a capsule. The tablet can be a single or multilayer tablet having compressed multiparticulate in one, all or none of the layers. Preferably, the dosage form is a controlled release dosage form. More preferably, it is a delayed release dosage form. The dosage form can be coated with a polymer, preferably a rate-controlling or a delayed release polymer. The polymer can also be compressed with the enhancer and drug to form a matrix dosage form such as a controlled release matrix dosage form. A polymer coating can then be applied to the matrix dosage form.

Other embodiments of the invention include the process of making the dosage forms, and methods for the treatment of a medical condition by administering the dosage forms to a patient and use of a drug and enhancer in the manufacture of a medicament.

IU) and NaC10; c) oral uncoated instant release tablet formulation containing USP heparin (90000 IU) and NaC8; and d) oral uncoated sustained release tablet formulation containing USP heparin (90000 IU) and sodium caprate prepared according to the invention as described in Example 2.

Figure 9:
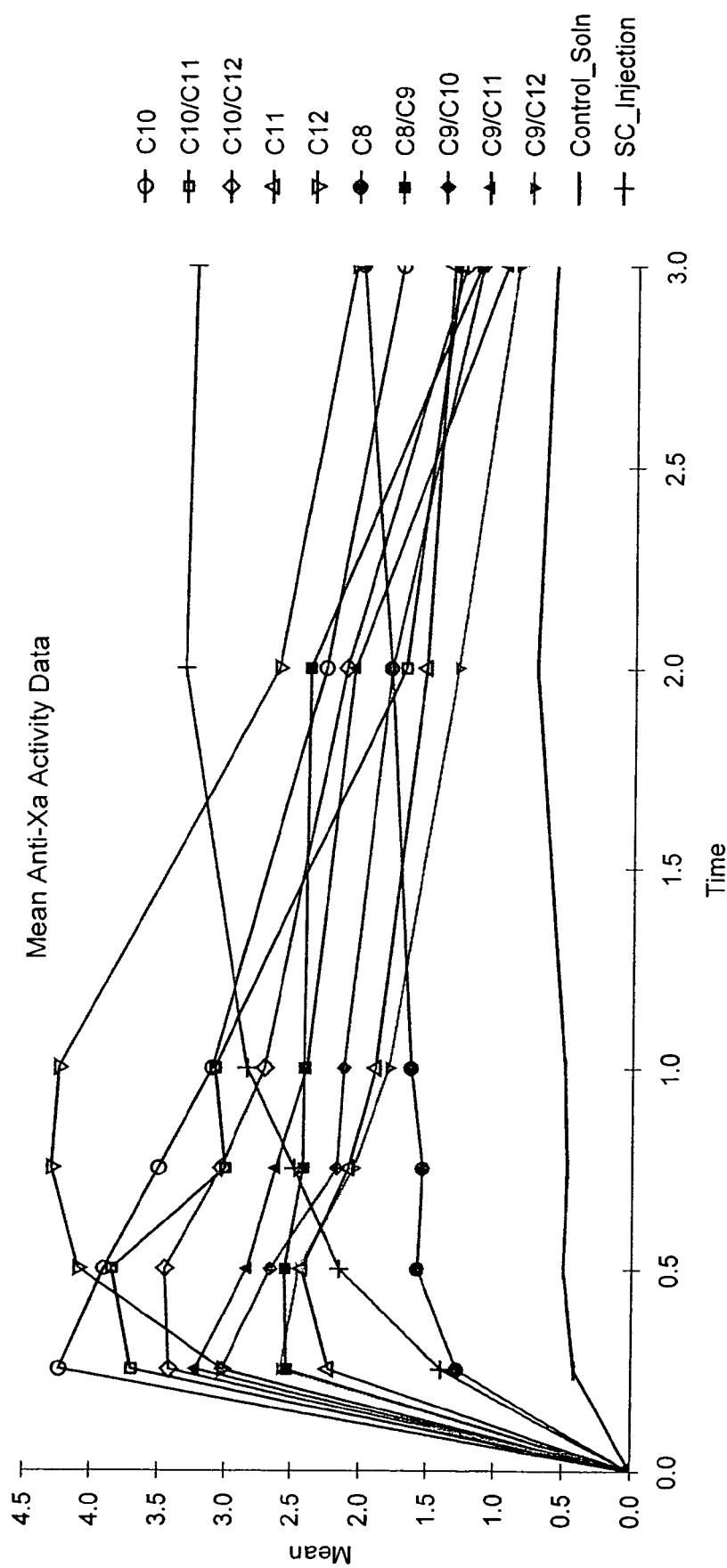

FIG. 9 shows the anti-factor $X_a$ response over a period of three hours following intraduodenal administration to rats of phosphate buffered saline solutions of parnaparin sodium (low molecular weight heparin (LMWH)) (1000 IU), in the presence of 35 mg of different enhancers such as sodium caprylate (C8), sodium nonanoate (C9), sodium caprate (C10), sodium undecanoate (C11), sodium laurate (C12) and different 50:50 binary mixtures of enhancers, to rats (n=8) in an open loop model. The reference product comprised administering 250 IU parnaparin sodium subcutaneously. The control solution comprised administering a solution containing 1000 IU parnaparin sodium without any enhancer intraduodenally.

Figure 10:
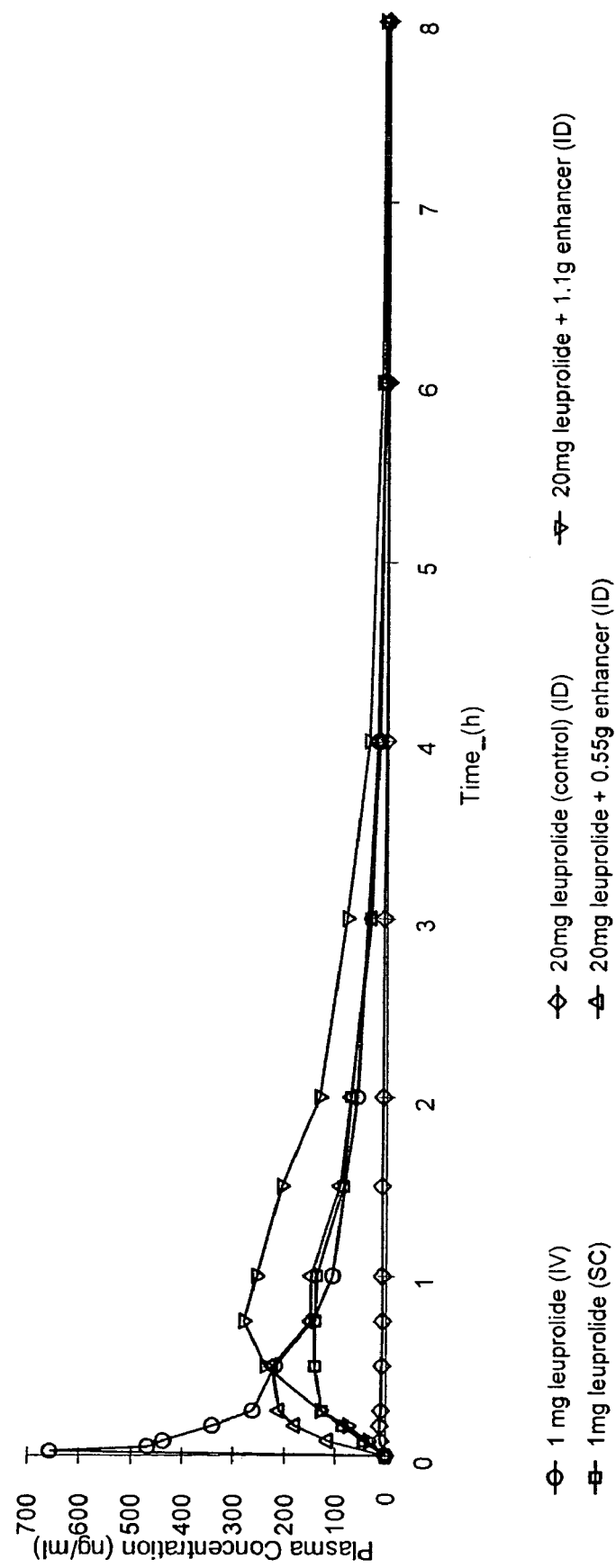

FIG. 10 shows the mean plasma levels of leuprolide over a period of eight hours following intraduodenal administration of solutions of leuprolide (20 mg) containing different levels of sodium caprate (0.0 g (control), 0.55 g, 1.1 g) to dogs.

Figure 11:
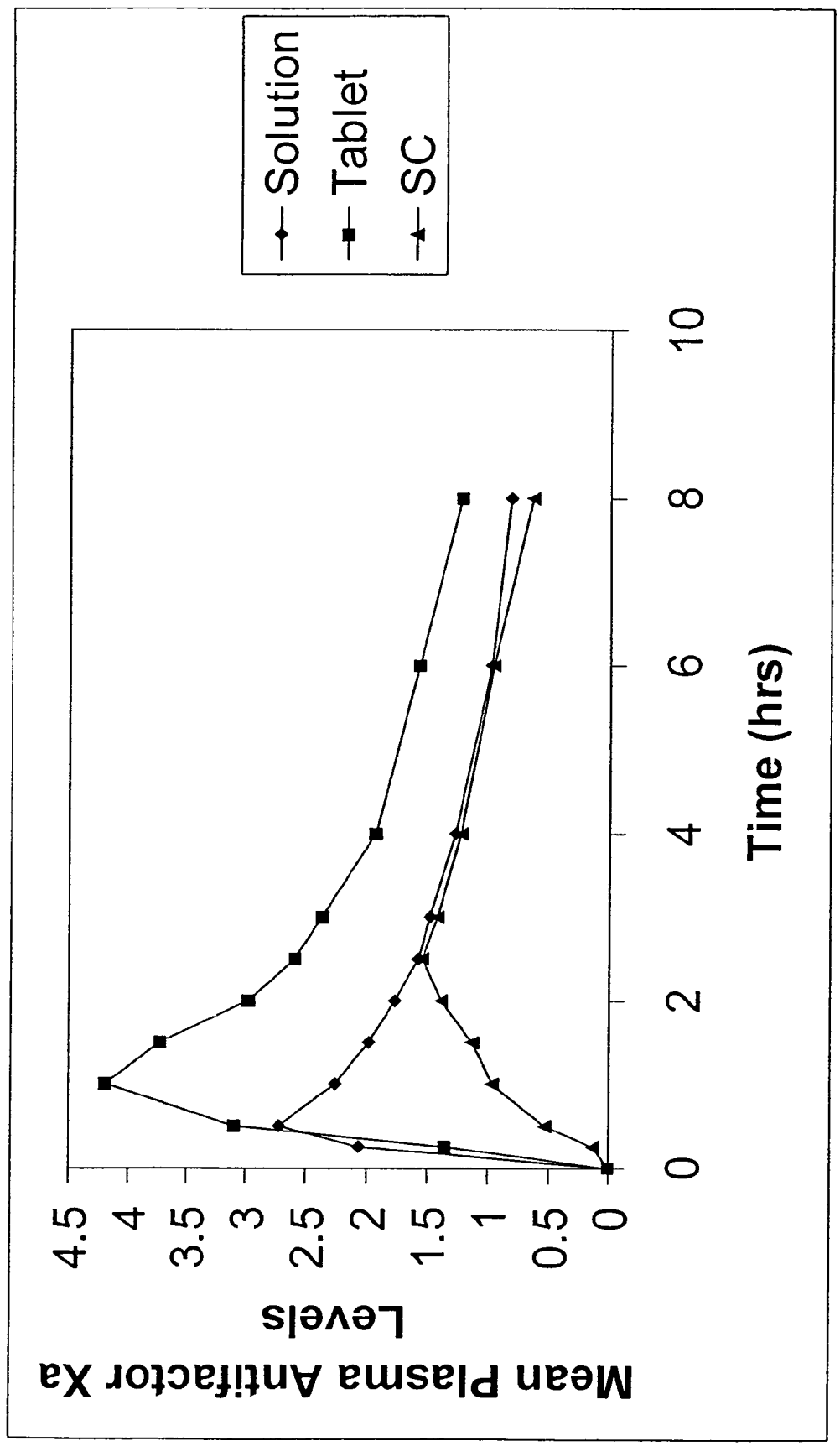

FIG. 11 shows the mean anti-factor $X_a$ response in dogs over a period of eight hours following oral administration of parnaparin sodium (90,000 IU) in the presence of 550 mg sodium caprate, as both a solution (10 ml) and an instant release tablet dosage form.

Figure 12:
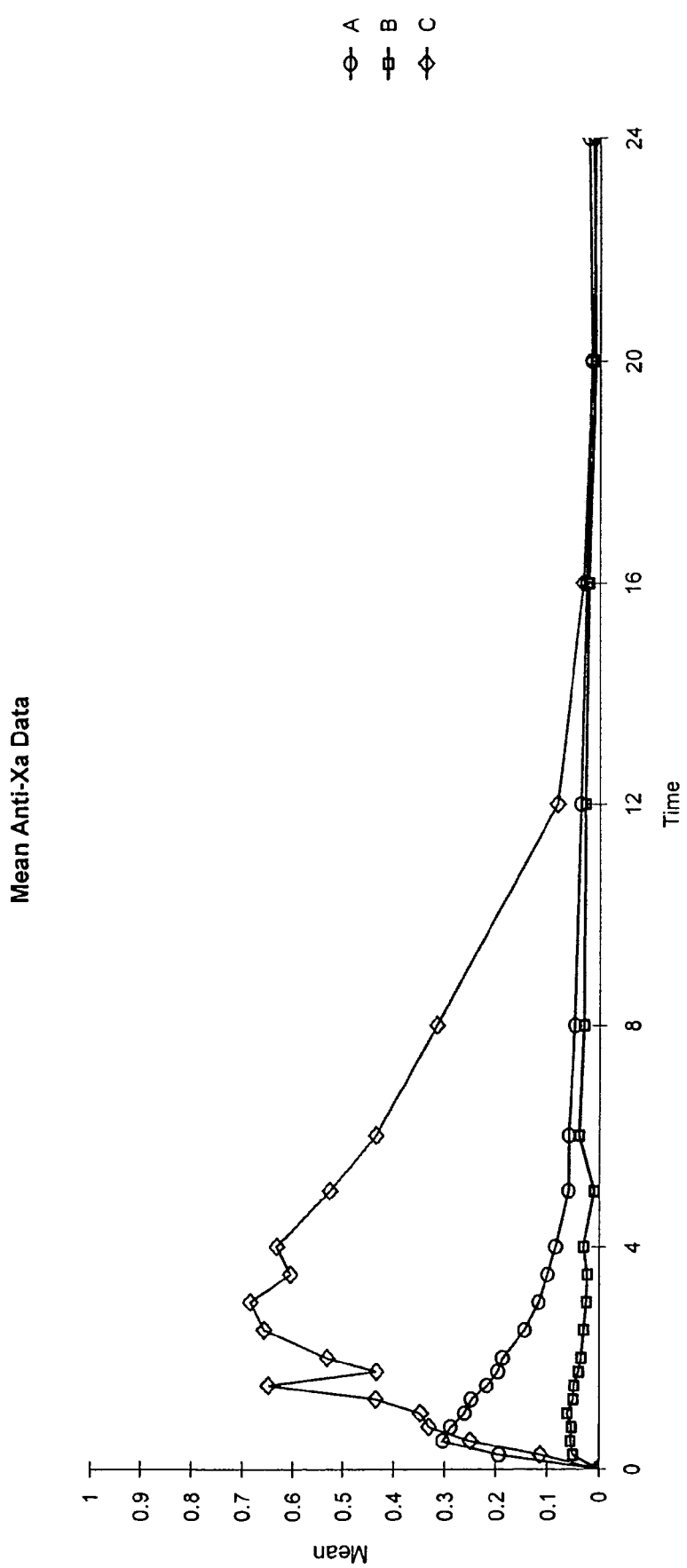
Figure 13:
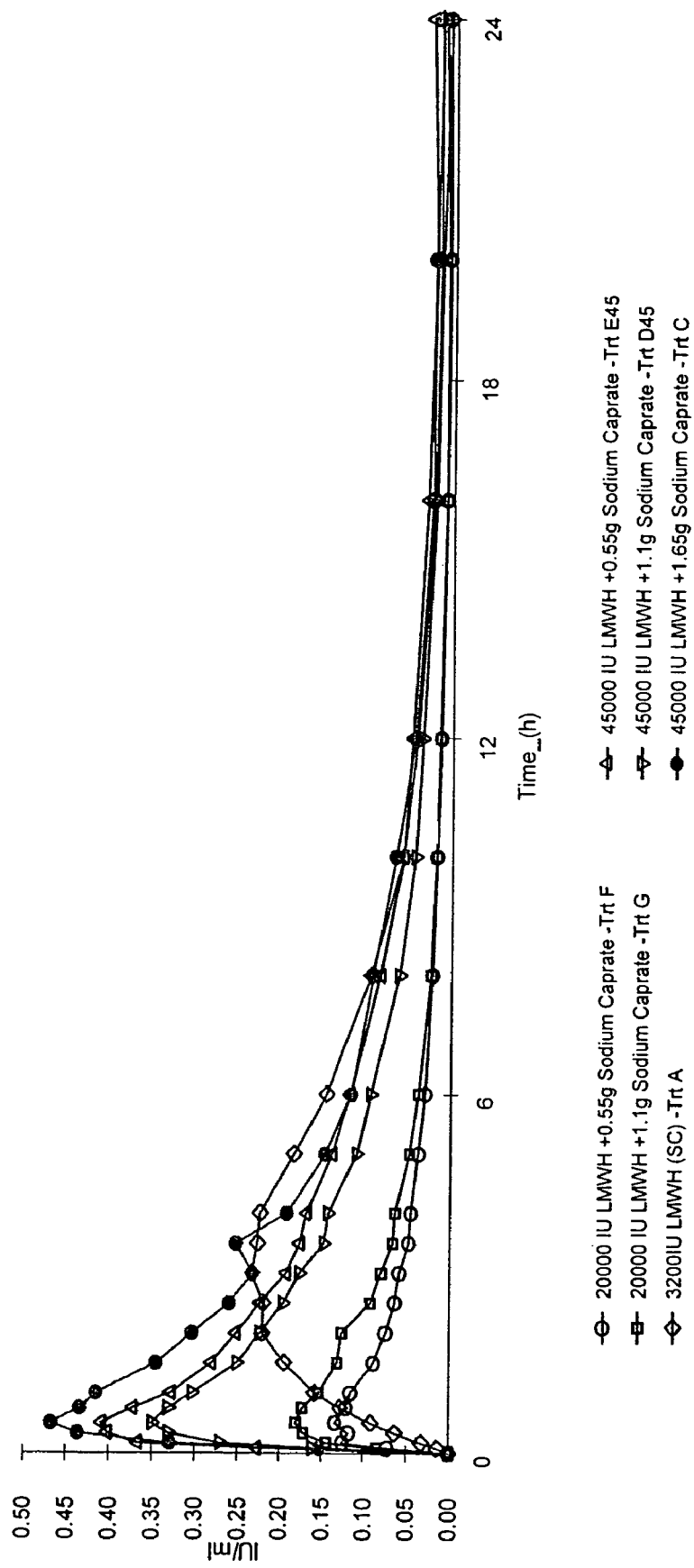

FIG. 12 shows the mean anti-factor $X_a$ response in humans over a period of 24 hours following oral administration of parnaparin sodium (90,000 IU) in the presence of sodium caprate, as both a solution (240 ml) and an instant release tablet dosage form FIG. 13 shows the mean anti-factor $X_a$ response in humans over a period of 24 hours following intrajejunal administration of 15 ml solutions containing different doses parnaparin sodium (20,000 IU, 45,000 IU, 90,000 IU) in the presence of different doses of sodium caprate (0.55 g, 1.1 g, 1.65 g)

Figure 14:
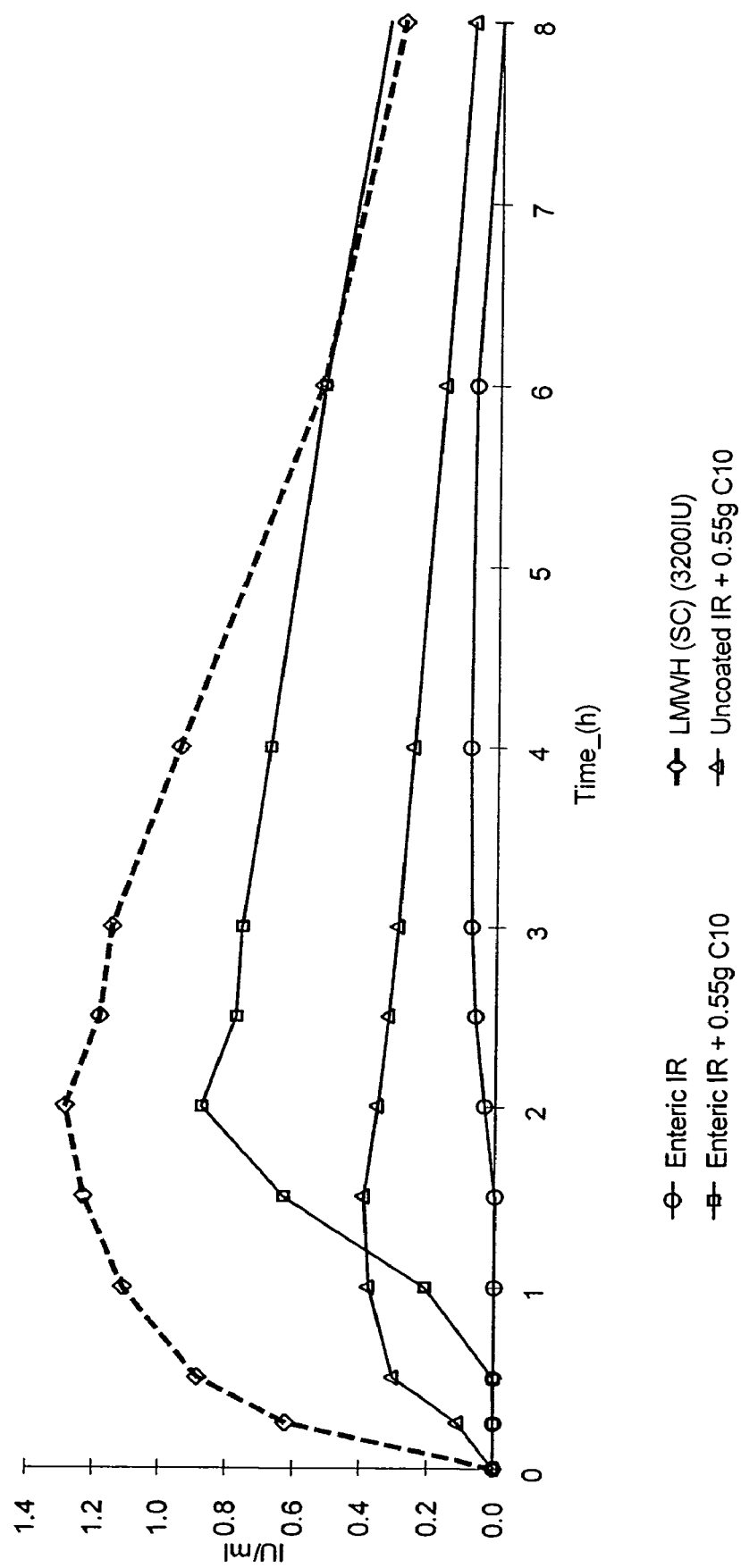

FIG. 14 shows the mean anti-factor $X_a$ response in dogs over a period of 8 hours following oral administration of 45,000 IU parnaparin sodium as: (a) instant release capsules containing 0.55 g sodium caprate, (b) Eudragit L coated rapidly disintegrating tablets containing 0.55 g sodium caprate and (c) Eudragit L coated rapidly disintegrating tablets without enhancer.

Figure 15:
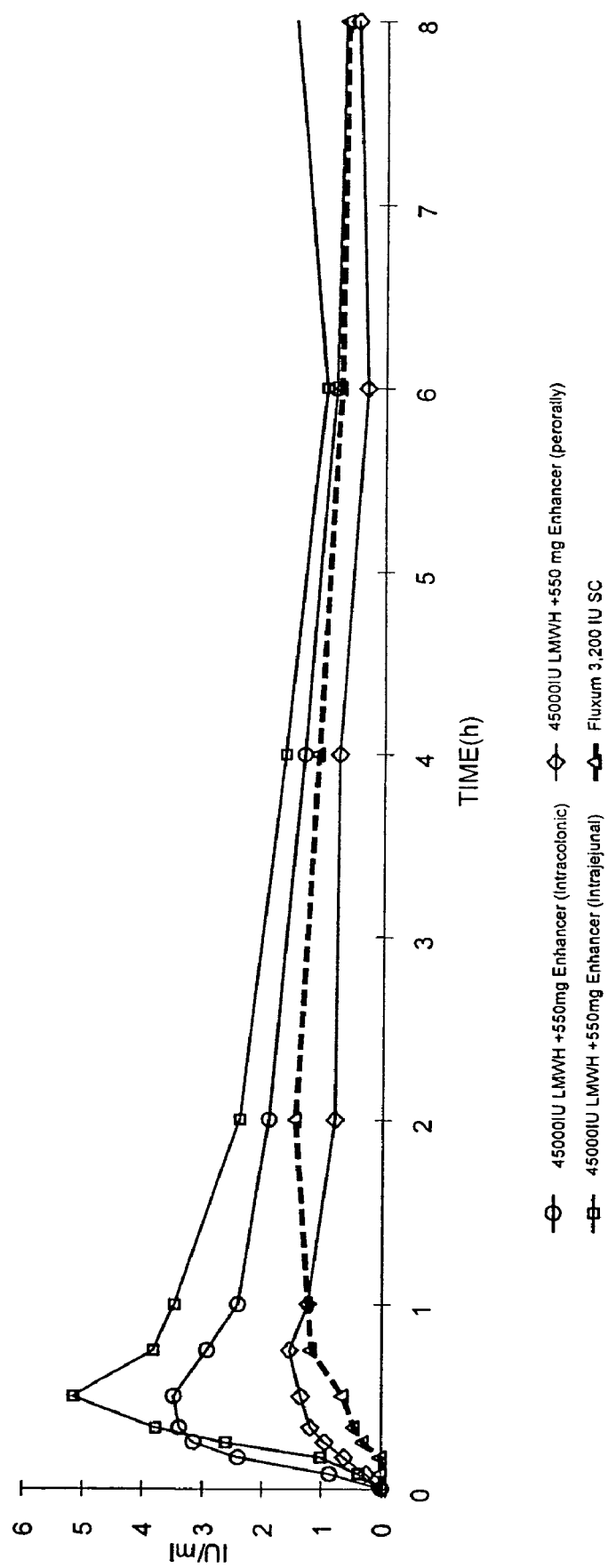

FIG. 15 shows the mean anti-factor $X_a$ response in dogs over a period of 8 hours following co-administration of 45,000 IU LMWH and 0.55 g sodium caprate orally, intrajejunally and intracolonically compared to subcutaneous administration.

Figure 16:
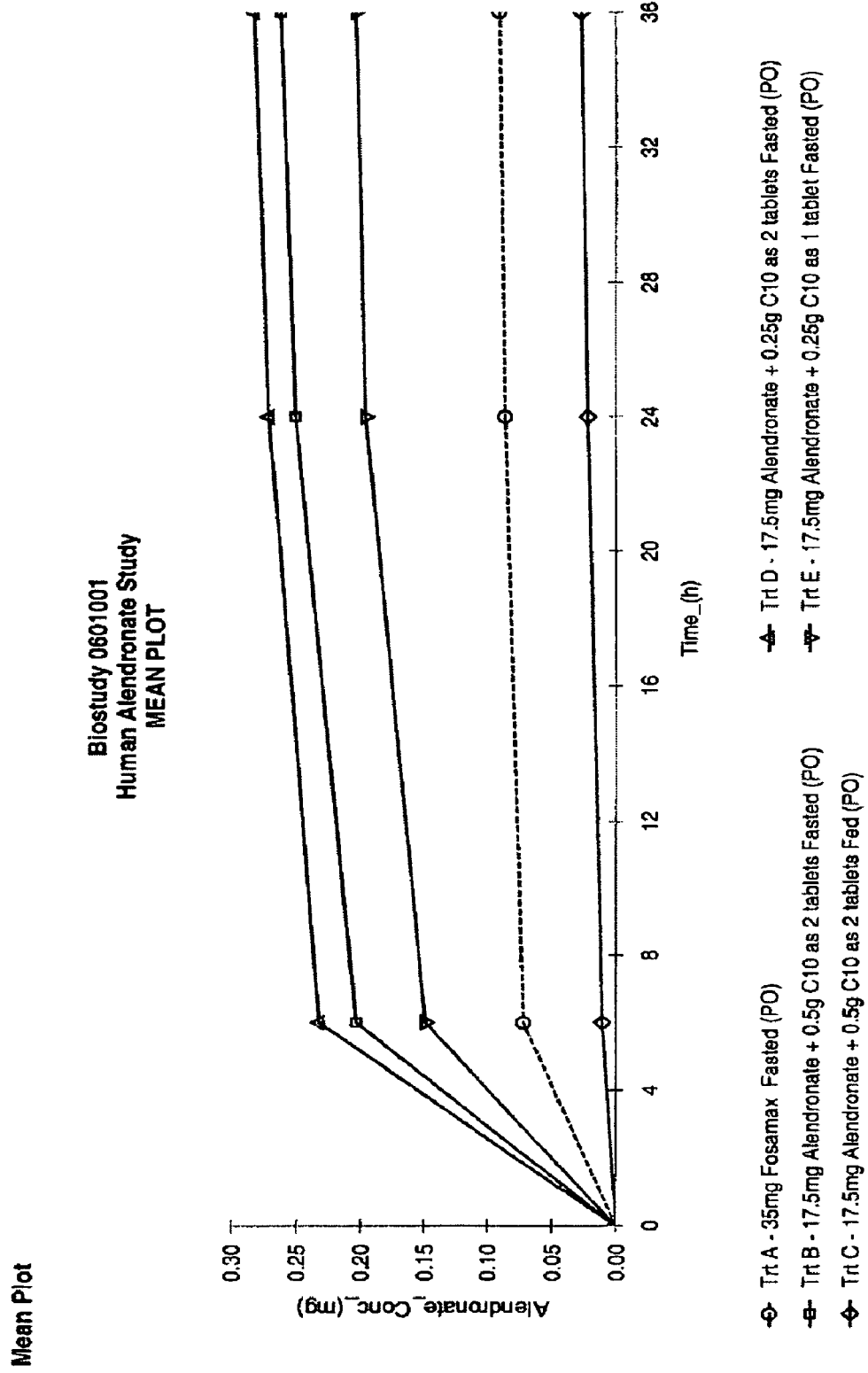

FIG. 16 shows the non-dose normalized amount of alendronate excreted in the urine over a period of 36 hours following oral administration of alendronate (17.5 mg) with different amounts of sodium caprate (0.5 g and 0.25 g) in the fasted and fed states compared with the mean plasma levels of Fosamax™ (35 mg) in the fasted state.

DETAILED DESCRIPTION OF THE INVENTION

As used in this specification and appended claims, the singular forms "a", "an" and "the" include plural referents unless the content clearly dictates otherwise. Thus, for example, reference to "an enhancer" includes a mixture of two or more enhancers, reference to "a drug" includes a mixture of two or more drugs, and the like.

As used herein, the term "drug" includes any drug, including conventional drugs and analogs thereof, appropriate for administration via the oral route to an animal including a human. The term "drug" also explicitly includes those entities that are poorly absorbed via the oral route including hydrophilic or macromolecular drugs such as peptides, proteins, oligosaccharides, polysaccharides or hormones including, but not limited to, insulin, calcitonin, calcitonin gene regulating protein, atrial natriuretic protein, colony stimulating factor, betaseron, erythropoietin (EPO), interferons, somatropin, somatotropin, somatostatin, insulin-like growth factor (somatomedins), luteinizing hormone releasing hormone (LHRH), tissue plasminogen activator (TPA), thyrotropin releasing hormone (TRH), growth hormone releasing hormone (GHRH), antidiuretic hormone (ADH) or vasopressin and analogues thereof such as for example desmopressin, parathyroid hormone (PTH), oxytocin, estradiol, growth hormones, leuprolide acetate, goserelin acetate, naferelin, buserelin, factor VIII, interleukins such as interleukin-2, and analogues thereof and anti-coagulant agents such as heparin, heparinoids, low molecular weight heparin, hirudin and analogues thereof, bisphosphonates including alendronate, clodronate, etidronate, incadronate, ibandronate, minodronate, pamidronate, risedronate, tiludronate and zoledronate, pentassacharides including anti-coagulant pentassacharides, antigens, adjuvants and the like. In those embodiments in which the drug is a bisphosphonate, the drug is selected from the group consisting of alendronate, clodronate, etidronate, incadronate, ibandronate, minodronate, pamidronate, risedronate, tiludronate and zoledronate. As used herein, the term "drug" includes all forms thereof including optically pure enantiomers or mixtures, racemic or otherwise, of enantiomers as well as derivative forms such as, for example, salts, acids, esters and the like. The drug may be provided in any suitable phase state including as a solid, liquid, solution, suspension and the like. When provided in solid particulate form, the particles may be of any suitable size or morphology and may assume one or more crystalline, semi-crystalline and/or amorphous forms.

The drug can be included in nano- or microparticulate drug delivery systems in which the drug is, or is entrapped within, encapsulated by, attached to, or otherwise associated with, a nano- or microparticle.

As used herein, a "therapeutically effective amount of a drug" refers to an amount of drug that elicits a therapeutically useful response in an animal, preferably a mammal, most preferably a human.

As used herein, the term "enhancer" refers to a compound (or mixture of compounds) which is capable of enhancing the transport of a drug, particularly a hydrophilic and/or macromolecular drug across the GIT in an animal such as a human, wherein the enhancer is a medium chain fatty acid or a medium chain fatty acid derivative having a carbon chain length of from 6 to 20 carbon atoms; with the provisos that (i) where the enhancer is an ester of a medium chain fatty acid, said chain length of from 6 to 20 carbon atoms relates to the chain length of the carboxylate moiety, and (ii) where the enhancer is an ether of a medium chain fatty acid, at least one alkoxy group has a carbon chain length of from 6 to 20 carbon atoms. Preferably, the enhancer is a sodium salt of a medium chain fatty acid. Most preferably, the enhancer is sodium caprate. In one embodiment, the enhancer is a solid at room temperature.

As used herein, the term "medium chain fatty acid derivative" includes fatty acid salts, esters, ethers, acid halides, amides, anhydrides, carboxylate esters, nitriles, as well as glycerides such as mono-, di- or tri-glycerides. The carbon chain may be characterized by various degrees of saturation. In other words, the carbon chain may be, for example, fully saturated or partially unsaturated (i.e. containing one or more carbon-carbon multiple bonds). The term "medium chain fatty acid derivative" is meant to encompass also medium chain fatty acids wherein the end of the carbon chain opposite the acid group (or derivative) is also functionalized with one of the above mentioned moieties (i.e., an ester, ether, acid halide, amide, anhydride, carboxylate esters, nitrile, or glyceride moiety). Such difunctional fatty acid derivatives thus include for example diacids and diesters (the functional moieties being of the same kind) and also difunctional compounds comprising different functional moieties, such as amino acids and amino acid derivatives, for example a medium chain fatty acid or an ester or a salt thereof comprising an amide moiety at the opposite end of the fatty acid carbon chain to the acid or ester or salt thereof.

As used herein, a "therapeutically effective amount of an enhancer" refers to an amount of enhancer that allows for uptake of therapeutically effective amounts of the drug via oral administration. It has been shown that the effectiveness of an enhancer in enhancing the gastrointestinal delivery of poorly permeable drugs is dependent on the site of administration (see Examples 6, 7 and 12), the site of optimum delivery being dependent on the drug and enhancer.

The enhancer of the present invention interacts in a transient and reversible manner with the GIT cell lining increasing permeability and facilitating the absorption of otherwise poorly permeable molecules. Preferred enhancers include (i) medium chain fatty acids and their salts, (l) medium chain fatty acid esters of glycerol and propylene glycol, and (iii) bile salts. In one embodiment, the enhancer is a medium chain fatty acid salt, ester, ether or other derivative of a medium chain fatty acid which is, preferably, solid at room temperature and which has a carbon chain length of from 8 to 14 carbon atoms; with the provisos that (i) where the enhancer is an ester of a medium chain fatty acid, said chain length of from 8 to 14 carbon atoms relates to the chain length of the carboxylate moiety, and (ii) where the enhancer is an ether of a medium chain fatty acid, at least one alkoxy group has a carbon chain length of from 8 to 14 carbon atoms. In another embodiment, the enhancer is a sodium salt of a medium chain fatty acid, the medium chain fatty acid having a carbon chain length of from 8 to 14 carbon atoms; the sodium salt being solid at room temperature. In a further embodiment, the enhancer is sodium caprylate, sodium caprate or sodium laurate. The drug and enhancer can be present in a ratio of from 1:100000 to 10:1 (drug:enhancer) preferably, from 1:1000 to 10:1.

As used herein, the term "rate controlling polymer material" includes hydrophilic polymers, hydrophobic polymers and mixtures of hydrophilic and/or hydrophobic polymers that are capable of controlling or retarding the release of the drug compound from a solid oral dosage form of the present invention. Suitable rate controlling polymer materials include those selected from the group consisting of hydroxyalkyl cellulose such as hydroxypropyl cellulose and hydroxypropyl methyl cellulose; poly(ethylene) oxide; alkyl cellulose such as ethyl cellulose and methyl cellulose; carboxymethyl cellulose, hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly (alkylmethacrylate) and poly(vinyl acetate). Other suitable hydrophobic polymers include polymers and/or copolymers derived from acrylic or methacrylic acid and their respective esters, zein, waxes, shellac and hydrogenated vegetable oils.

Particularly useful in the practice of the present invention are poly acrylic acid, poly acrylate, poly methacrylic acid and poly methacrylate polymers such as those sold under the Eudragit® trade name (Rohm GmbH, Darmstadt, Germany) specifically Eudragit® L, Eudragit® S, Eudragit® RL, Eudragit® RS coating materials and mixtures thereof. Some of these polymers can be used as delayed release polymers to control the site where the drug is released. They include polymethacrylate polymers such as those sold under the Eudragit® trade name (Rohm GmbH, Darmstadt, Germany) specifically Eudragit® L, Eudragit® S, Eudragit® RL, Eudragit® RS coating materials and mixtures thereof.

A solid oral dosage form according to the present invention may be a tablet, a multiparticulate or a capsule. A preferred solid oral dosage form is a delayed release dosage form which minimizes the release of drug and enhancer in the stomach, and hence the dilution of the local enhancer concentration therein, and releases the drug and enhancer in the intestine. A particularly preferred solid oral dosage form is a delayed release rapid onset dosage form. Such a dosage form minimizes the release of drug and enhancer in the stomach, and hence the dilution of the local enhancer concentration therein, but releases the drug and enhancer rapidly once the appropriate site in the intestine has been reached, maximizing the delivery of the poorly permeable drug by maximizing the local concentration of drug and enhancer at the site of absorption.

As used herein, the term "tablet" includes, but is not limited to, immediate release (IR) tablets, sustained release (SR) tablets, matrix tablets, multilayer tablets, multilayer matrix tablets, extended release tablets, delayed release tablets and pulsed release tablets any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms particularly useful in the practice of the invention include those selected from the group consisting of IR tablets, SR tablets, coated IR tablets, matrix tablets, coated matrix tablets, multilayer tablets, coated multilayer tablets, multilayer matrix tablets and coated multilayer matrix tablets. A preferred tablet dosage form is an enteric coated tablet dosage form. A particularly preferred tablet dosage form is an enteric coated rapid onset tablet dosage form.

As used herein, the term "capsule" includes instant release capsules, sustained release capsules, coated instant release capsules, coated sustained release capsules, delayed release capsules and coated delayed release capsules. In one embodiment, the capsule dosage form is an enteric coated capsule dosage form. In another embodiment, the capsule dosage form is an enteric coated rapid onset capsule dosage form.

The term "multiparticulate" as used herein means a plurality of discrete particles, pellets, mini-tablets and mixtures or combinations thereof. If the oral form is a multiparticulate capsule, hard or soft gelatin capsules can suitably be used to contain the multiparticulate. Alternatively a sachet can suitably be used to contain the multiparticulate. The multiparticulate may be coated with a layer containing rate controlling polymer material. The multiparticulate oral dosage form may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule. In one embodiment, the multiparticulate dosage form comprises a capsule containing delayed release rapid onset minitablets. In another embodiment, the multiparticulate dosage form comprises a delayed release capsule comprising instant release minitablets. In a further embodiment, the multiparticulate dosage form comprises a capsule comprising delayed release granules. In yet another embodiment, the multiparticulate dosage form comprises a delayed release capsule comprising instant release granules.

In another embodiment, the multiparticulate together with one or more auxiliary excipient materials may be compressed into tablet form such as a single layer or multilayer tablet. Typically, a multilayer tablet may comprise two layers containing the same or different levels of the same active ingredient having the same or different release characteristics. Alternatively, a multilayer tablet may contain different active ingredient in each layer. Such a tablet, either single layered or multilayered, can optionally be coated with a controlled release polymer so as to provide additional controlled release properties.

A number of embodiments of the invention will now be described. In each case the drug may be present in any amount which is sufficient to elicit a therapeutic effect. As will be appreciated by those skilled in the art, the actual amount of drug compound used will depend on, among other things, the potency of the drug, the specifics of the patient and the therapeutic purpose for which the drug is being used. The amount of drug compound may suitably be in the range of from about 0.5 µg to about 1000 mg. The enhancer is suitably present in any amount sufficient to allow for uptake of therapeutically effective amounts of the drug via oral administration. In one embodiment, the drug and the enhancer are present in a ratio of from 1:100000 to 10:1 (drug:enhancer). In another embodiment, the ratio of drug to enhancer is from 1:1000 to 10:1. The actual ratio of drug to enhancer used will depend on, among other things, the potency of the particular drug and the enhancing activity of the particular enhancer.

In one embodiment, there is provided a pharmaceutical composition and a solid oral dosage form made therefrom comprising a bisphosphonate and, as an enhancer to promote absorption of the bisphosphonate at the GIT cell lining, a medium chain fatty acid or a medium chain fatty acid derivative having a carbon chain length of from 6 to 20 carbon atoms, wherein the enhancer and the composition are solids at room temperature.

In another embodiment, there is provided a pharmaceutical composition and an oral dosage form made therefrom comprising a bisphosphonate and, as an enhancer to promote absorption of the bisphosphonate at the GIT cell lining, wherein the only enhancer present in the composition is a medium chain fatty acid or a medium chain fatty acid derivative having a carbon chain length of from 6 to 20 carbon atoms.

In a further embodiment, there is provided a multilayer tablet comprising a composition of the present invention. Typically such a multilayer tablet may comprise a first layer containing a drug and an enhancer in an instant release form and a second layer containing a drug and an enhancer in a modified release form. As used herein, the term "modified release" includes sustained, delayed, or otherwise controlled release of a drug upon administration to a patient. In an alternative embodiment, a multilayer tablet may comprise a first layer containing a drug and a second layer containing an enhancer. Each layer may independently comprise further excipients chosen to modify the release of the drug or the enhancer. Thus the drug and the enhancer may be released from the respective first and second layers at rates which are the same or different. Alternatively, each layer of the multilayer tablet may comprise both drug and enhancer in the same or different amounts.

In yet another embodiment, there is provided a multiparticulate comprising a composition of the present invention. The multiparticulate may comprise particles, pellets minitablets or combinations thereof, and the drug and the enhancer may be contained in the same or different populations of particles, pellets or mini-tablets making up the multiparticulate. In multiparticulate embodiments, sachets and capsules such as hard or soft gelatin capsules can suitably be used to contain the multiparticulate. A multiparticulate dosage form may comprise a blend of two or more populations of particles, pellets or mini-tablets having different in vitro and/or in vivo release characteristics. For example, a multiparticulate dosage form may comprise a blend of an immediate release component and a delayed release component contained in a suitable capsule.

In the case of any of the above-mentioned embodiments, a controlled release coating may be applied to the final dosage form (capsule, tablet, multilayer tablet etc.). The controlled release coating may typically comprise a rate controlling polymer material as defined above. The dissolution characteristics of such a coating material may be pH dependent or independent of pH.

The various embodiments of the solid oral dosage forms of the invention may further comprise auxiliary excipient materials such as, for example, diluents, lubricants, disintegrants, plasticizers, anti-tack agents, opacifying agents, pigments, flavorings and the like. As will be appreciated by those skilled in the art, the exact choice of excipients and their relative amounts will depend to some extent on the final dosage form.

Suitable diluents include for example pharmaceutically acceptable inert fillers such as microcrystalline cellulose, lactose, dibasic calcium phosphate, saccharides, and/or mixtures of any of the foregoing. Examples of diluents include microcrystalline cellulose such as that sold under the Avicel trademark (FMC Corp., Philadelphia, Pa.) for example Avicel™ pH101, Avicel™ pH102 and Avicel™ pH112; lactose such as lactose monohydrate, lactose anhydrous and Pharmatose DCL21; dibasic calcium phosphate such as Emcompress® (JRS Pharma, Patterson, N.Y.); mannitol; starch; sorbitol; sucrose; and glucose. Suitable lubricants, including agents that act on the flowability of the powder to be compressed are, for example, colloidal silicon dioxide such as Aerosil™ 200; talc; stearic acid, magnesium stearate, and calcium stearate. Suitable disintegrants include for example lightly cross-linked polyvinyl pyrrolidone, corn starch, potato starch, maize starch and modified starches, croscarmellose sodium, cross-povidone, sodium starch glycolate and combinations and mixtures thereof.

Example 1

TRH Containing Tablets (a) Caco-2 Monolayers.

Cell Culture: Caco-2 cells were cultured in Dulbecco's Modified Eagles Medium (DMEM) 4.5 g/L glucose supplemented with 1% (v/v) non-essential amino acids; 10% fetal calf serum and 1% penicillin/streptomycin. The cells were cultured at 37° C. and 5% $CO_2$ in 95% humidity. The cells were grown and expanded in standard tissue culture flasks and were passaged once they attained 100% confluence. The Caco-2 cells were then seeded on polycarbonate filter inserts (Costar; 12 mm diameter, 0.4 μm pore size) at a density of $5\times10^5$ cells/cm² and incubated in six well culture plates with a medium change every second day. Confluent monolayers between day 20 and day 30 seeding on filters and at passages 30-40 were used throughout these studies.

Transepithelial Transport Studies: The effects of sodium salts of various MCFAs on the transport of ³H-TRH (apical to basolateral flux) was examined as follows: 15.0 μCi/ml (0.2 μM) ³H-TRH was added apically at time zero for TRH flux experiments. The transport experiments were performed in Hank's Balanced Salt Solution (HBSS) containing 25 mM N-[2-hydroxyethyl]-piperazine-N'-[2-ethanesulfonic acid] (HEPES) buffer, pH 7.4 at 37° C. Due to variations in solubilities, various concentrations of the different MCFA sodium salts and various apical buffers were used as shown in Table 1. In all cases the basolateral chamber contained regular HBSS+HEPES.

TABLE 1

Concentrations and buffers used for various MCFA sodium salts

| MCFA salt* | Conc. (mM) | Buffer |
| --- | --- | --- |
| NaC8:0 | 0.32 | HBSS + HEPES |
| NaC10:0 | 0.40 | Ca²⁺ free HBSS |
| NaC12:0 | 3.77 | PBS** |
| NaC14:0 | 1.44 | PBS** |
| NaC18:0 | 0.16 | HBSS + HEPES |
| NaC18:2 | 0.16 | HBSS + HEPES |

*In the nomenclature CX:Y for a MCFA salt, X indicates the length of the carbon chain and Y indicates the position of unsaturation, if any.
**PBS—phosphate buffer solution.

After removing the cell culture medium, the monolayers were placed in wells containing prewarmed HBSS (37° C.); 1 ml apically and 2 ml basolaterally. Monolayers were incubated at 37° C. for 30 mins. Then at time zero, apical HBSS was replaced with the relevant apical test solution containing the radiolabelled compounds with and without the enhancer compound. Transepithelial electrical resistance (TEER) of the monolayer was measured at time zero and at 30 min intervals up to 120 min using a Millicell ERS chopstix apparatus (Millipore (U.K.) Ltd., Hertfordshire, UK) with Evom to monitor the integrity of the monolayer. The plates were placed on an orbital shaker in an incubator (37° C.). Transport across the monolayers was followed by basolateral sampling (1 ml) at 30 min. intervals up to 120 mins. At each 30 min. interval each insert was transferred to a new well containing 2 ml fresh prewarmed HBSS. Apical stock radioactivity was determined by taking 10 μl samples at t=0 and t=120 mins. Scintillation fluid (10 ml) was added to each sample and the disintegrations per min. of each sample were determined in a Wallac System 1409 scintillation counter. Mean values for ³H-TRH concentrations were calculated for the apical and basolateral solutions at each time point. The apparent permeability coefficients were calculated using the method described by Artursson (Artursson P., J. Pharm. Sci. 79:476-482 (1990)).

Figure 1:
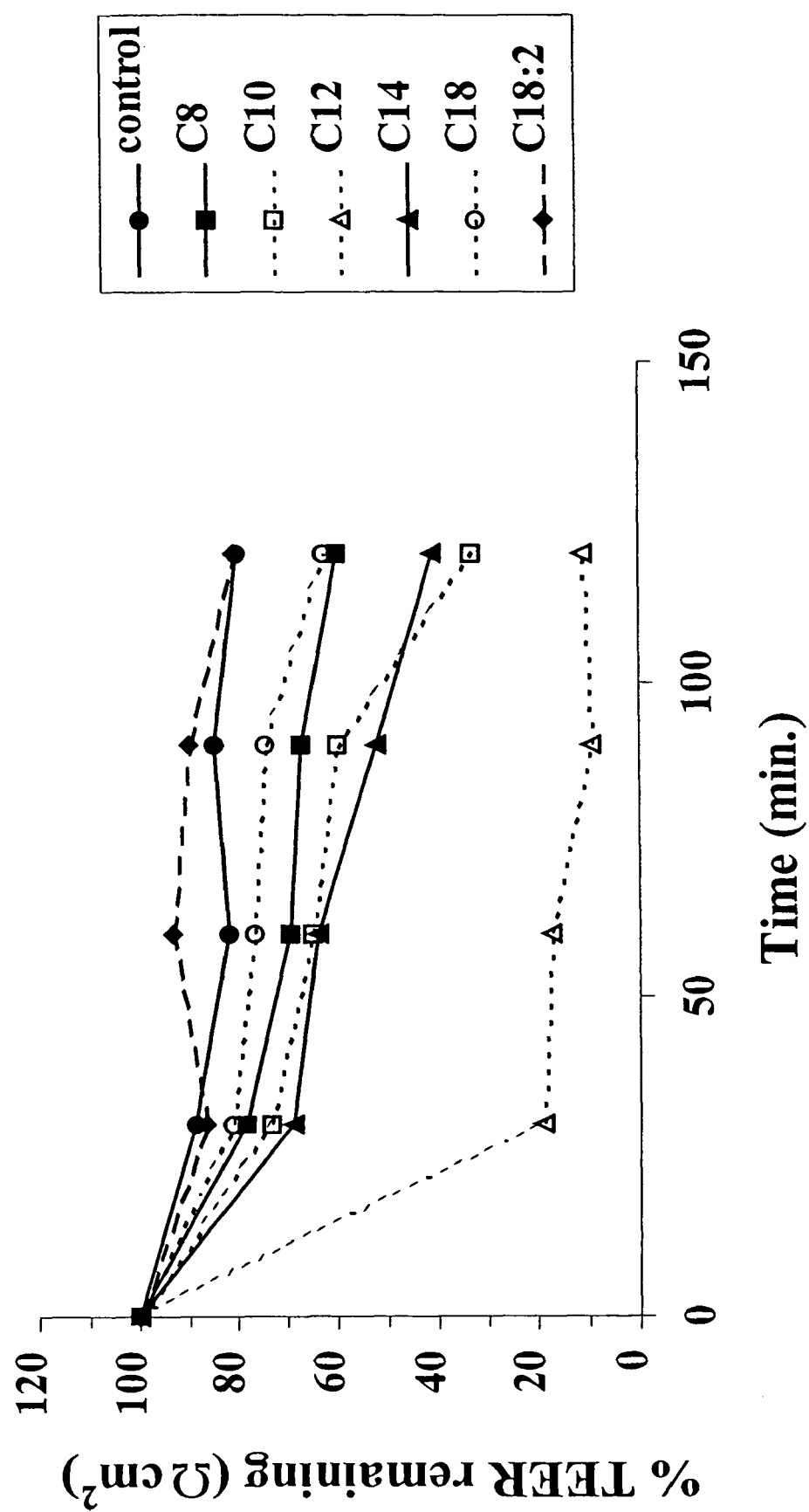
FIG. 1 shows the effect of the sodium salts of C8, C10, C12, C14, C18 and C18:2 with $^3$H-TRH on TEER ($\Omega cm^2$) in Caco-2 monolayers at time 0 and at 30 min. intervals up to 2 hours as described in Example 1.

FIG. 1 shows the effect of C8, C10, C12, C14, C18 and C18:2 sodium salts with ³H-TRH on TEER (Ωcm²) in Caco-2 monolayers over 2 hours. The data for the C8, C10, C14 and C18 indicate minimal reduction in TEER compared to the control. While the data for C12 indicates some cell damage (reduction in TEER), this reduction is probably a result of the higher concentration of enhancer used in this.

Figure 2:
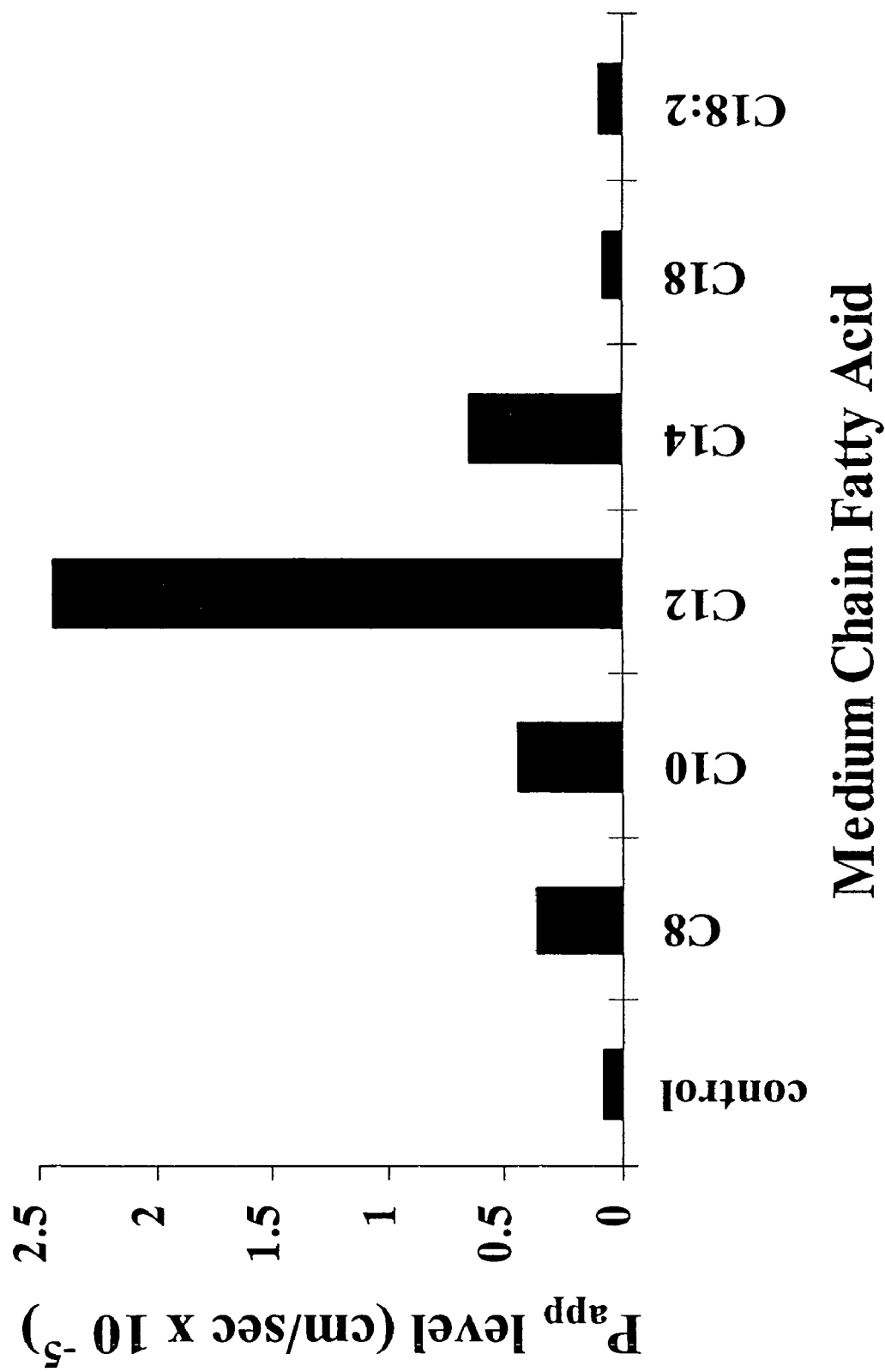
FIG. 2 shows the effect of the sodium salts of C8, C10, C12, C14, C18 and C18:2 on $P_{app}$ for $^3$H-TRH transport in Caco-2 monolayers as described in Example 1.

FIG. 2 shows the effect of C8, C10, C12, C14, C18 and C18:2 sodium salts on $P_{app}$ for ³H-TRH across in Caco-2 monolayers. Compared to the control, the sodium salts of C8, C10, C12 and C14 showed considerable increases in the permeability constant, $P_{app}$, at the concentrations used. It is noted that the high $P_{app}$ value observed for the C12 salt may be indicative of cell damage at this high enhancer concentration.

Mitochondrial Toxicity Assay: Mitochondrial dehydrogenase (MDH) activity was assessed as a marker of cell viability using a method based on the color change of tetrazolium salt in the presence MDH. Cells were harvested, counted and seeded on 96 well plates at an approximate density of $10^6$ cells/ml (100 μl of cell suspension per well). The cells were then incubated at 37° C. for 24 hours in humidified atmosphere, 5% $CO_2$. A number of wells were treated with each MCFA sodium salt solution at the concentrations shown in Table 1 and the plate was incubated for 2 hours. After incubation 10 μl of MTT labeling reagent was added to each well for 4 hours. Solubilization buffer (100 μl; see Table 1) was added to each well and the plate was incubated for a further 24 hours. Absorbance at 570 nm of each sample was measured using a spectrophotometer (Dynatech MR7000).

(b) In Vivo Administration (Closed Loop Rat Model).

In vivo rat closed loop studies were modified from the methods of Doluisio et al. (Doluisio J. T., et al: Journal of Pharmaceutical Science (1969), 58, 1196-1200) and Brayden et al. (Brayden D.: Drug Delivery Pharmaceutical News (1997) 4(1)). Male Wistar rats (weight range 250 g-350 g) were anaesthetized with ketamine hydrochloride/acepromazine. A mid-line incision was made in the abdomen and a segment of the duodenum (7-9 cm of tissue) was isolated about 5 cm distal from the pyloric sphincter, taking care to avoid damage to surrounding blood vessels. The sample solutions (PBS containing C8 or C10 (35 mg) and TRH (500 μg and 1000 μg)) and control (PBS containing TRH only (500 μg and 1000 μg)) warmed to 37° C. were administered directly into the lumen of the duodenal segment using a 26 G needle. All intraduodenal dose volumes (for samples and control) were 1 ml/kg. The proximal end of the segment was ligated and the loop was sprayed with isotonic saline (37° C.) to provide moisture and then replaced in the abdominal cavity avoiding distension. The incision was closed with surgical clips. A group of animals were administered TRH in PBS (100 μg in 0.2 ml) by subcutaneous injection as a reference.

Figure 3:
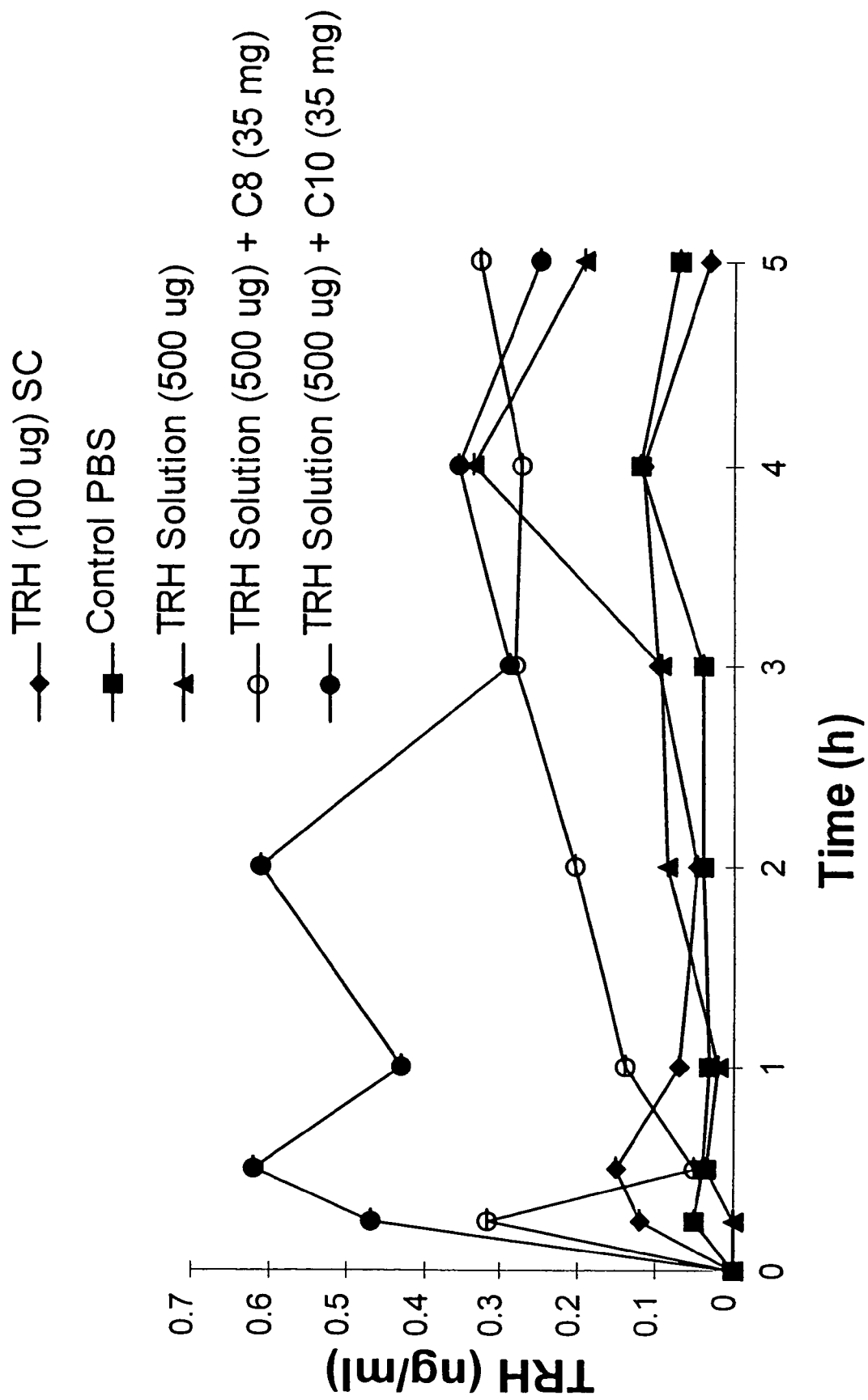
FIG. 3 shows the serum TRH concentration-time profiles following interduodenal bolus dose of 500 µg TRH with NaC8 or NaC10 (35 mg) enhancer present according to the closed loop rat model described in Example 1.
Figure 4:
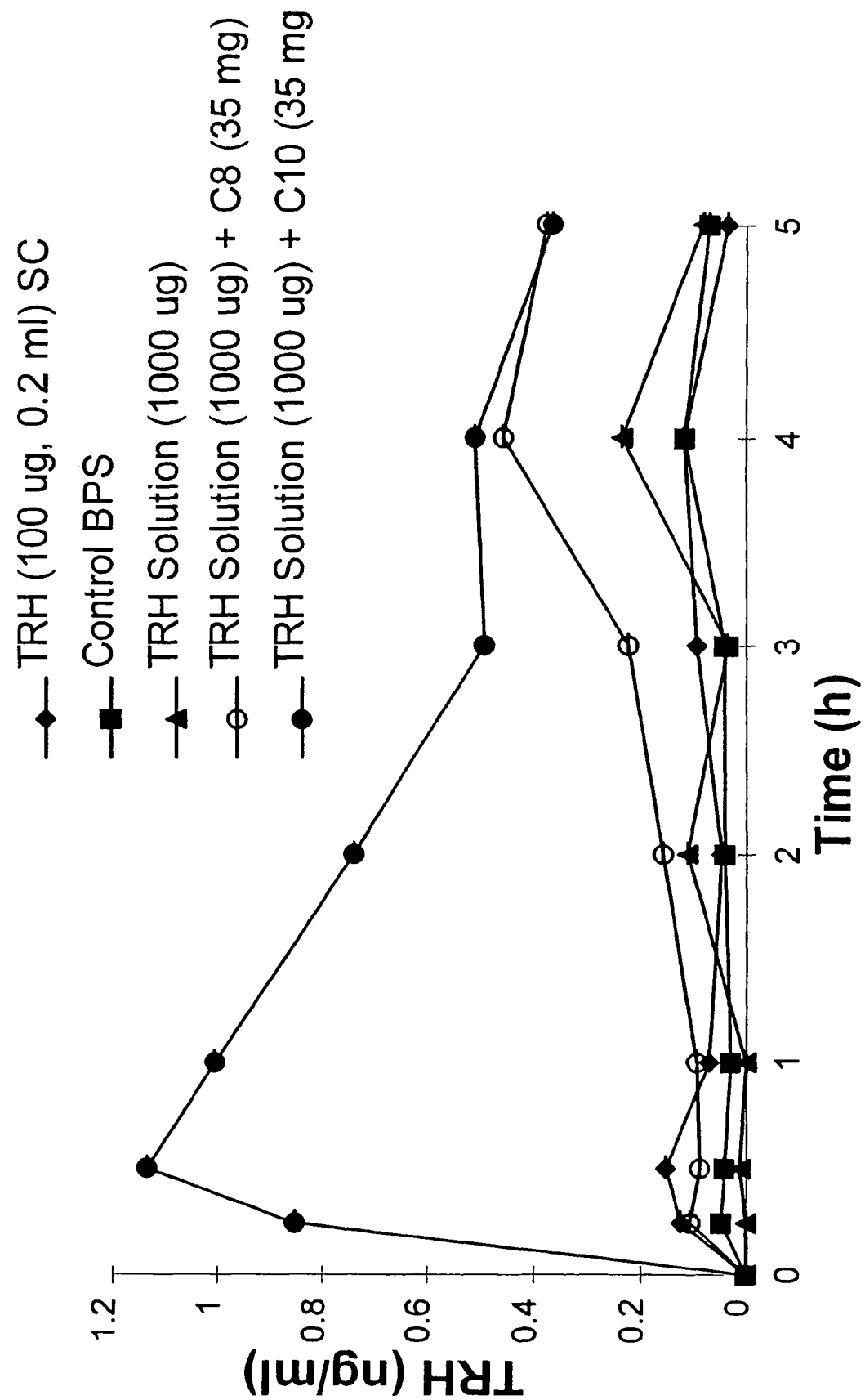
FIG. 4 shows the serum TRH concentration-time profiles following interduodenal bolus dose of 1000 µg TRH with NaC8 or NaC10 (35 mg) enhancer present according to the closed loop rat model described in Example 1.

FIG. 3 shows the serum TRH concentration-time profiles following interduodenal bolus dose of 500 μg TRH with NaC8 or NaC10 (35 mg) enhancer present, according to the closed loop rat model. FIG. 4 shows the serum TRH concentration-time profiles following interduodenal bolus dose of 1000 μg TRH with NaC8 or NaC10 (35 mg) enhancer present, according to the closed loop rat model. From FIGS. 3 and 4 it can be seen that the presence of the enhancer in each case significantly increases the serum levels of TRH over the control TRH solution indicating increased absorption of the drug in the presence of the enhancer.

(c) Tableting.

Having established the enhancing effect of NaC8 and NaC10 on TRH in solution, immediate release (IR) and sustained release (SR) TRH tablets and the like may be prepared. IR and SR formulations are detailed in Tables 2 and 3 below.

TABLE 2

THR IR tablet formulation details (all amounts in wt. %)

| TRH | NaC$_8$ | NaC10 | Silica Dioxide | Mag. Stearate | Lactose | Disintegrant | Micro. Cellulose | PVP |
|---|---|---|---|---|---|---|---|---|
| 0.64 | 70.36 | — | 0.5 | 0.5 | 20 | 8 | — | — |
| 1.27 | 69.73 | — | 0.5 | 0.5 | 20 | 8 | — | — |
| 1.23 | — | 67.64 | 0.5 | 0.5 | 20 | 8 | — | 2.13 |
| 2.42 | — | 66.45 | 0.5 | 0.5 | — | 8 | 20 | 2.13 |
| 2.42 | — | 66.45 | 0.5 | 0.5 | 20 | 8 | — | 2.13 |

TABLE 3

THR SR tablet formulation details (all amounts in wt. %)

| TRH | NaC$_{10}$ | Silica Dioxide | Magnesium Stearate | HPMC$^{(a)}$ | Microcystalline Cellulose | PVP |
|---|---|---|---|---|---|---|
| 1.41 | 77.59 | 0.5 | 0.5 | 20 | — | — |
| 1.05 | 57.95 | 0.5 | 0.5 | 20 | 20 | — |
| 2.68 | 73.94 | 0.5 | 0.5 | 20 | — | 2.37 |

Example 2

Heparin Containing Tablets (a) Closed-Loop Rat Segment.

Figure 5:
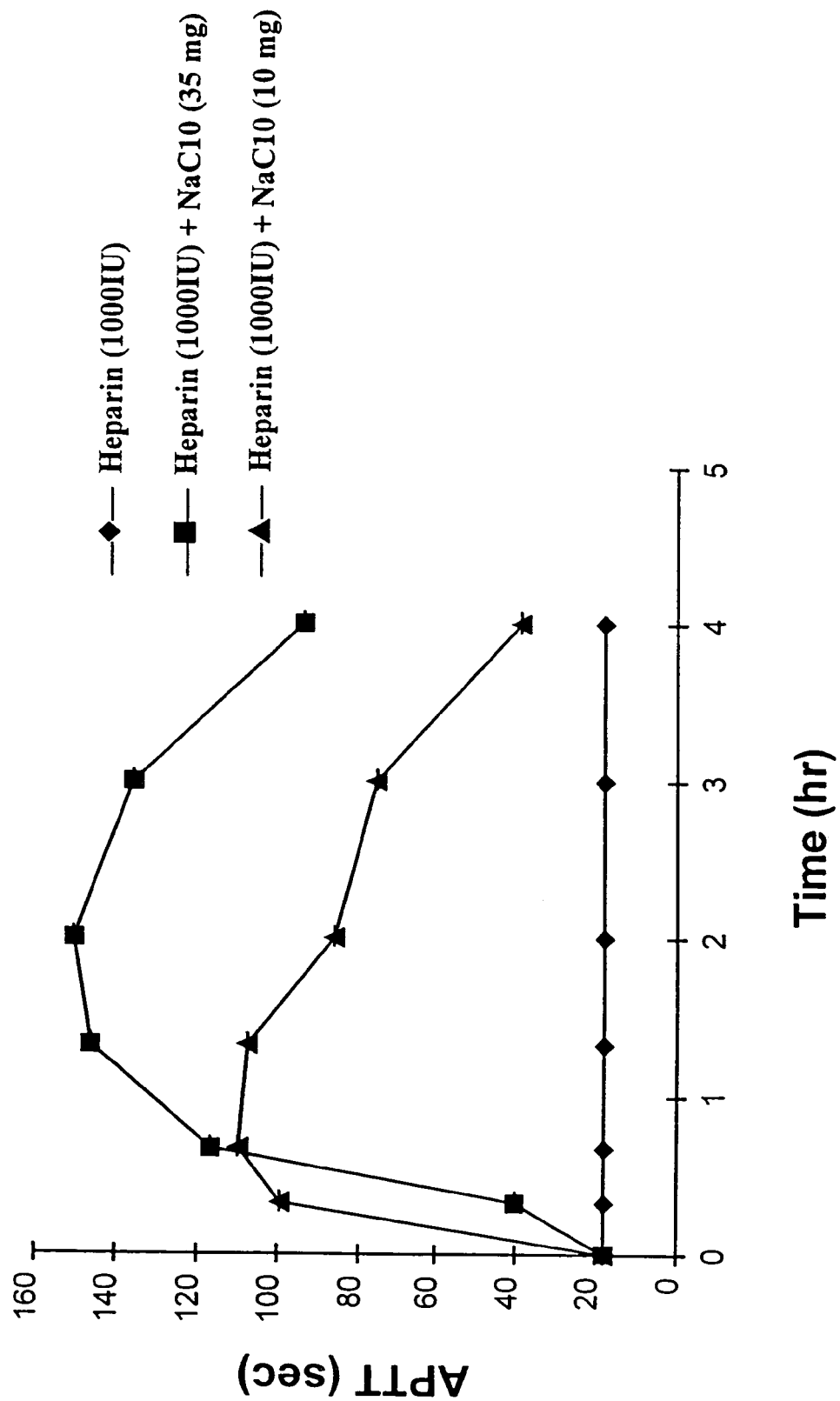
FIG. 5 shows the APTT response over a period of 4 hours following administration of USP heparin (1000 IU) with different sodium caprate (C10) levels (10 and 35 mg) according to the closed loop rat model described in Example 2.

The procedure carried out in Example 1 (a) above was repeated using USP heparin in place of TRH and dosing intraileally rather than intraduodenally. A mid-line incision was made in the abdomen and the distal end of the ileum located (about 10 cm proximal to the ileo-caecal junction). 7-9 cm of tissue was isolated and the distal end ligated, taking care to avoid damage to surrounding blood vessels. Heparin absorption as indicated by activated prothrombin time (APTT) response was measured by placing a drop of whole blood (freshly sampled from the tail artery) on the test cartridge of Biotrack 512 coagulation monitor. APTT measurements were taken at various time points. FIG. 5 shows the APTT response of USP heparin (1000 iu) at different sodium caprate (C10) levels (10 and 35 mg). Using APTT response as an indicator of heparin absorption into the bloodstream, it is clear that there is a significant increase in absorption in the presence of sodium caprate compared to the control heparin solution containing no enhancer.

Figure 6:
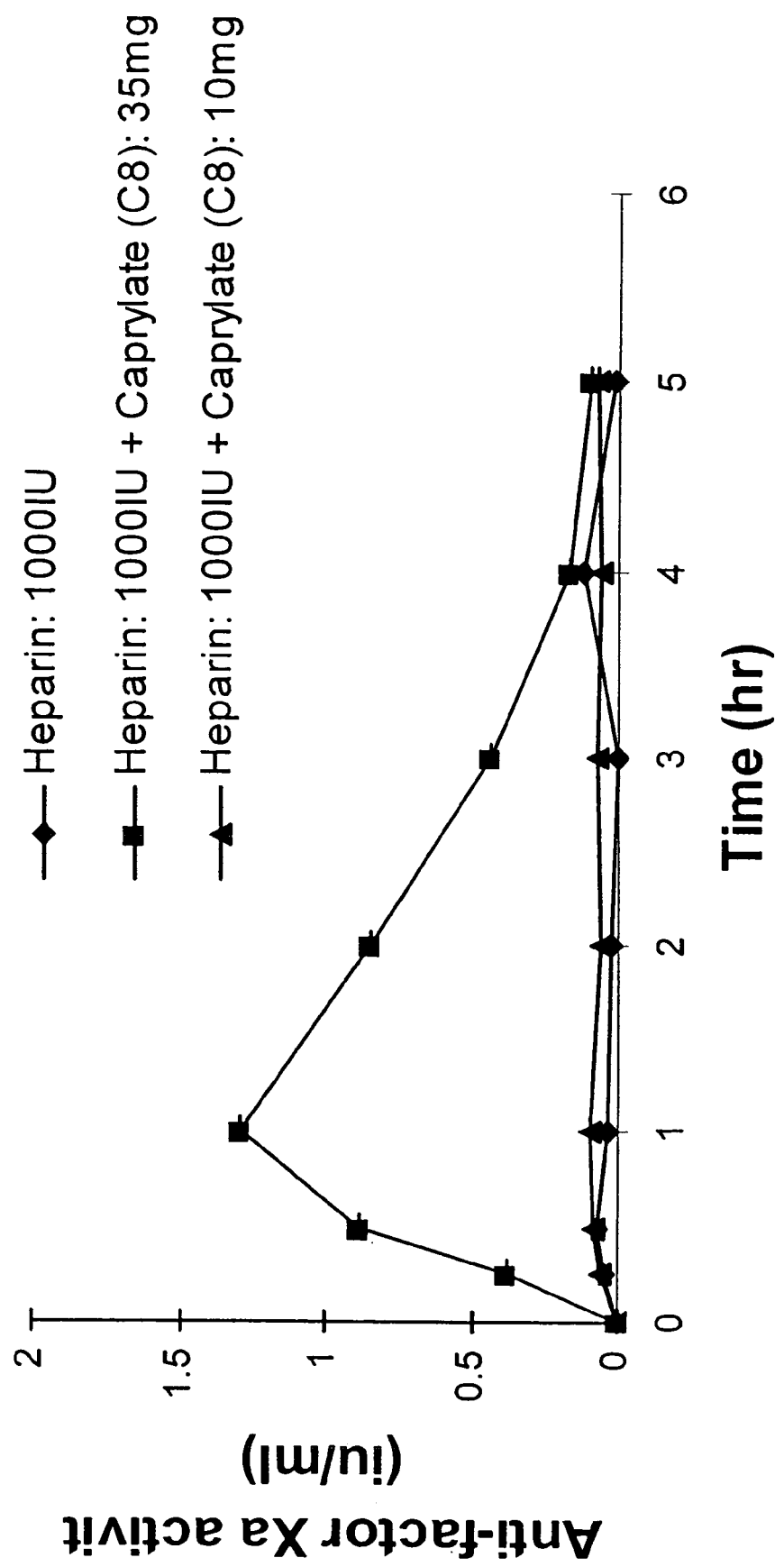
FIG. 6 shows the anti-factor $X_a$ response over a period of 5 hours following administration of USP heparin (1000 IU) in the presence of different sodium caprylate (C8) levels (10 mg and 35 mg) according to the closed loop rat model described in Example 2.
Figure 7:
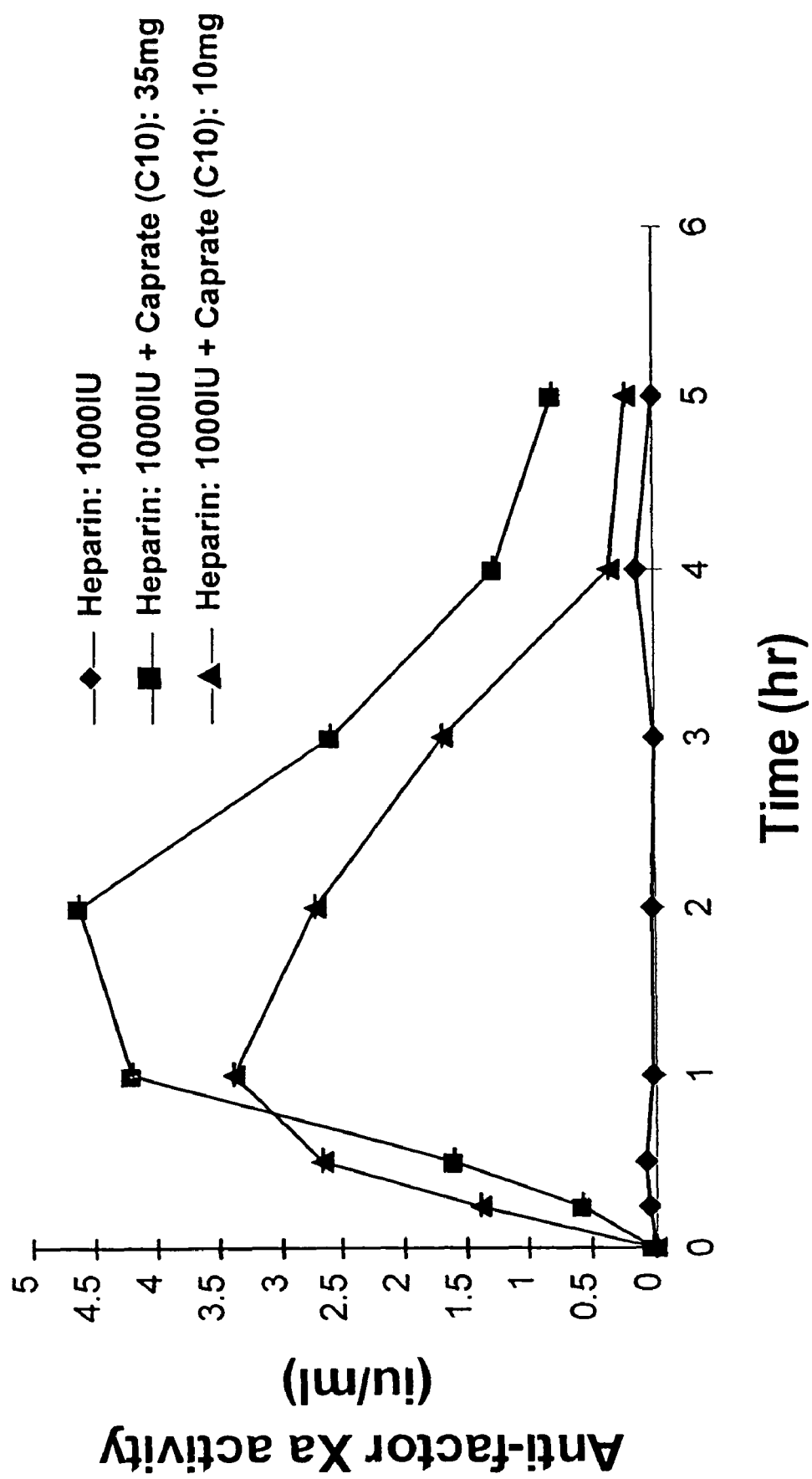
FIG. 7 shows the anti-factor $X_a$ response over a period of five hours following administration of USP heparin (1000 IU) in the presence of different sodium caprate (C10) levels (10 mg and 35 mg) according to the closed loop rat model described in Example 2.

Citrated blood samples were centrifuged at 3000 rpm for 15 mins. to obtain plasma for anti-factor $X_a$ analysis. FIG. 6 shows the anti-factor $X_a$ response of USP heparin (1000 iu) in the presence of sodium caprylate (C8, 10 mg and 35 mg). FIG. 7 shows the anti-factor $X_a$ response of USP heparin (1000 iu) in the presence of sodium caprate (C10, 10 mg and 35 mg). The control in each case is a solution of the same heparin concentration containing no enhancer. The significant increase in anti-factor $X_a$ activity observed for NaC8 (at 35 mg dose) and NaC10 (at both 10 mg and 35 mg doses) is indicative of the increase in heparin absorption relative to the control heparin solution.

(b) Tableting.

(i) IR Tablets.

Instant release (IR) tablets containing heparin sodium USP (197.25 IU/mg, supplied by Scientific Protein Labs., Waunkee, Wis.) and an enhancer (sodium caprylate, NaC8; sodium caprate, NaC10, supplied by Napp Technologies, New Jersey) were prepared according to the formulae detailed in Table 4 by direct compression of the blend using a Manesty (E) single tablet press. The blend was prepared as follows: heparin, the enhancer and tablet excipients (excluding where applicable colloidal silica dioxide and magnesium stearate) were weighed out into a container. The colloidal silica dioxide, when present, was sieved through a 425 μm sieve into the container, after which the mixture was blended for four minutes before adding the magnesium stearate and blending for a further one minute.

TABLE 4

Formulation data for IR tablets containing heparin and enhancer (all amounts in wt. %)

| Batch No. | NaC$_8$ | NaC$_{10}$ | Heparin | Silica dioxide | Magnesium stearate | Mannitol | Disintegrant$^{(a)}$ | PVP$^{(b)}$ |
|---|---|---|---|---|---|---|---|---|
| 1 | 65.7 | — | 13.3 | 0.5 | 0.5 | 20.0 | — | — |
| 2 | 62.2 | — | 16.8 | 0.5 | 0.5 | 20.0 | — | — |
| 3 | 57.49 | — | 21.91 | 0.1 | 0.5 | 20.0 | — | — |
| 4 | 75.66 | — | 15.34 | 0.5 | 0.5 | — | 8.0 | — |
| 5 | — | 62.0 | 37.5 | 0.5 | — | — | — | — |
| 6 | — | 49.43 | 30.07 | 0.5 | — | 20.0 | — | — |
| 7 | — | 31.29 | 25.94 | 0.5 | 0.5 | 40.0 | — | 1.77 |

"—" indicates "not applicable"
$^{(a)}$Disintegrant used was sodium starch glycolate;
$^{(b)}$PVP = polyvinyl pyrrolidone The potency of tablets prepared above was tested using a heparin assay based on the azure dye determination of heparin. The sample to be assayed was added to an Azure A dye solution and the heparin content was calculated from the absorbance of the sample solution at 626 nm. Tablet data and potency values for selected batches detailed in Table 4 are given in Table 5.

Dissolution profiles for IR tablets according to this Example in phosphate buffer at pH 7.4 were determined by heparin assay, sampling at various time points.

Heparin/sodium caprylate: Tablets from batches 1 and 2 gave rapid release yielding 100% of the drug compound at 15 minutes. Tablets from batch 4 also gave rapid release yielding 100% release at 30 minutes.

Heparin/sodium caprate: Tablets from batches 5 and 6 gave rapid release 100% of the drug compound at 15 minutes.

TABLE 5

Tablet data and potency values for IR heparin tablets

| Batch No. | Enhancer | Tablet Weight (mg) | Hardness (N) | Disintegration Time(s) | Actual heparin Potency (mg/g) | Potency As % of label |
|---|---|---|---|---|---|---|
| 1 | $NaC_8$ | 431 ± 5 | 85 + 4 | — | 145.675 | 109 |
| 2 | $NaC_8$ | 414 ± 14 | 82 ± 9 | — | 175.79 | 105 |
| 3 | $NaC_8$ | 650 ± 4 | 71 ± 12 | 552 | 166.4 | 119 |
| 4 | $NaC_8$ | 377 ± 2 | 58 ± 10 | — | 168.04 | 110 |
| 5 | $NaC_{10}$ | 408 ± 21 | 79 ± 7 | — | 394.47 | 105 |
| 6 | $NaC_{10}$ | 490 ± 6 | 124 ± 10 | — | 323.33 | 108 |
| 7 | $NaC_{10}$ | 584 ± 12 | 69 ± 22 | 485 | 143.0 | 102 |

(ii) SR Tablets.

Using the same procedure as used in (i) above, sustained release (SR) tablets were prepared according to the formulae shown in Table 6. The potency of controlled release tablets was determined using the same procedure as in (i) above. Tablet details and potency for selected batches are shown in Table 7.

Dissolution profiles for SR tablets according this Example were determined by heparin assay at pH 7.4, sampling at various time points.

Heparin/sodium caprylate: Dissolution data for batches 8, 9 and 11 are shown in Table 8. From this data it can be seen that heparin/sodium caprylate SR tablets with 15% Methocel K100LV with and without 5% sodium starch glycolate (batches 8 & 9) gave a sustained release with 100% release occurring between 3 and 4 hours. Batch 11 sustaining 10% mannitol gave a faster release.

Heparin/sodium caprate: Dissolution data for batches 13 and 14 are shown in Table 8. From this data it can be seen that heparin/sodium caprate SR tablets with 20% Methocel K100LV (batch 13) gave a sustained release of the drug compound over a six hour period. Where Methocel K15M (batch 14) was used in place of Methocel K100LV release of the drug compound was incomplete after 8 hours.

TABLE 7

Table data and Potency values for SR heparin tablets

| Batch No. | Enhancer | Tablet Weight (mg) | Hardness (N) | Disintegration Time (s) | Actual Heparin potency (mg/g) |
|---|---|---|---|---|---|
| 8 | $NaC_8$ | 397 ± 5 | 52 ± 11 | — | — |
| 9 | $NaC_8$ | 436 ± 11 | 40 ± 10 | — | 140.08 |
| 10 | $NaC_8$ | 384 ± 4 | 42 ± 12 | — | — |
| 11 | $NaC_8$ | 400 ± 8 | 72 ± 16 | — | 129.79 |
| 12 | $NaC_8$ | 683 ± 9 | 84 ± 17 | 3318 | 147.10 |
| 13 | $NaC_{10}$ | 491 ± 14 | 69 ± 7 | — | — |
| 14 | $NaC_{10}$ | 456 ± 13 | 47 ± 4 | — | — |
| 15 | $NaC_{10}$ | 470 ± 29 | — | 2982 | 148.20 |

TABLE 8

Dissolution data for selected batches of SR tablets

| | % Release (as of label) | | | | |
|---|---|---|---|---|---|
| Time (min) | Batch 8 ($NaC_8$) | Batch 9 ($NaC_8$) | Batch 11 ($NaC_8$) | Batch 13 ($NaC_{10}$) | Batch 14 ($NaC_{10}$) |
| 0 | 0 | 0 | 0 | 0 | 0 |
| 15 | 22.9 | 21.2 | 45.3 | 18.8 | 5.7 |
| 30 | 37.3 | 30.8 | 72.3 | 45.0 | 11.6 |
| 60 | 57.8 | 54.5 | 101.9 | 44.8 | 11.2 |
| 120 | 92.2 | 90.8 | 109.4 | 65.2 | 20.0 |
| 240 | 109.5 | 105.8 | 96.4 | 83.1 | 33.9 |
| 360 | — | — | — | 90.3 | 66.0 |
| 480 | — | — | — | 102.7 | 82.8 |

(iii) Enteric Coated Tablets.

Tablets from batches 7 and 15 were enterically coated with a coating solution as detailed in Table 9. Tablets were coated with 5% w/w coating solution using a side vented coating pan (Freund Hi-Coater). Disintegration testing was carried out in a VanKel disintegration tester VK100E4635. Disintegration medium was initially simulated gastric fluid pH1.2 for one hour and then phosphate buffer pH7. The disintegration time recorded was the time from introduction into phosphate buffer pH7.4 to complete disintegration. The disintegration time for enterically coated tablets from batch 7 was 34 min. 24 sec, while for enteric coated tablets from batch 15 the disintegration time was 93 min. 40 sec.

TABLE 6

Formulation data for SR tablets containing heparin and enhancer
(all amounts in wt. %)

| Batch No. | $NaC_8$ | $NaC^{10}$ | Heparin | Silica dioxide | Mg. stearate | HPMC[a] | Disintegrant[b] | Mannitol | Micro. cellulose | PVP[c] |
|---|---|---|---|---|---|---|---|---|---|---|
| 8 | 69.84 | — | 14.16 | 0.5 | 0.5 | 15 | — | — | — | — |
| 9 | 65.68 | — | 13.32 | 0.5 | 0.5 | 15 | 5.0 | — | — | — |
| 10 | 65.68 | — | 13.32 | 0.5 | 0.5 | 12 | 8.0 | — | — | — |
| 11 | 65.68 | — | 13.32 | 0.5 | 0.5 | 10.0 | — | 10.0 | — | — |
| 12 | 53.77 | — | 20.48 | — | 1.0 | 14.85 | — | — | 9.9 | — |
| 13 | — | 56.2 | 23.3 | 0.5 | — | 20.0 | — | — | — | — |
| 14 | — | 56.2 | 23.3 | 0.5 | — | 20.0* | — | — | — | — |
| 15 | — | 41.63 | 34.52 | 0.5 | 1.0 | 20.0 | — | — | — | 2.35 |

"—" indicates "not applicable";
[a]Hydroxypropylmethyl cellulose: Methocel K100LV in each case except "*" in which Methocel K15M was employed;
[b]Disintegrant used was sodium starch glycolate;
[c]PVP = polyvinyl pyrrolidone;

TABLE 9

| Enteric coating solution | |
|---|---|
| Component | Amount (wt. %) |
| Eudragit ® 12.5 | 49.86 |
| Diethylphthlate | 1.26 |
| Isopropyl alcohol | 43.33 |
| Talc | 2.46 |
| Water | 3.06 |

(c) Dog Study.

Figure 8:
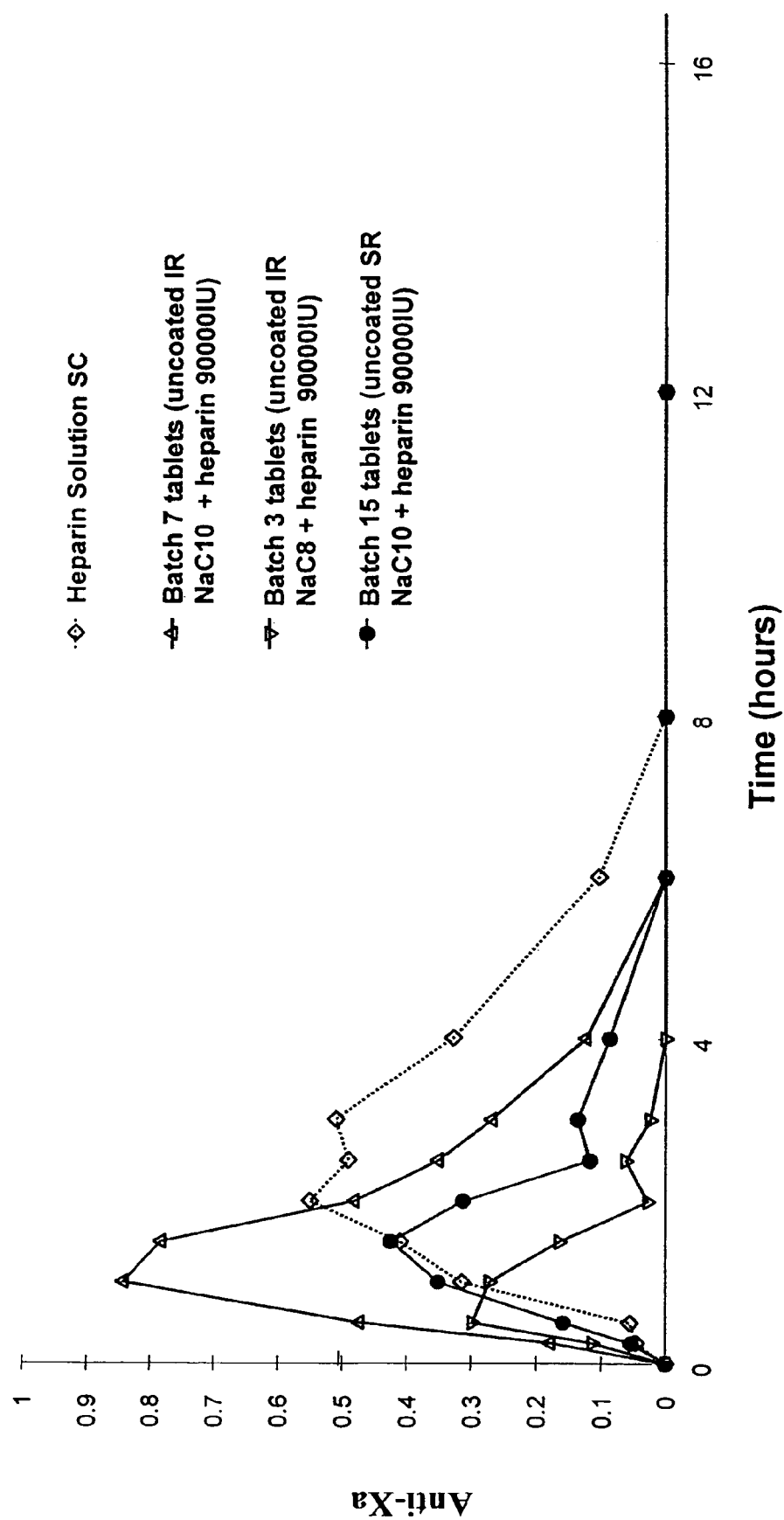
FIG. 8 shows the mean anti-factor $X_a$ response in dogs over a period of time up to 8 hours following administration of: a) s.c. USP heparin solution (5000 IU); b) oral uncoated instant release tablet formulation containing USP heparin (90000

Tablets from batches 3, 7 and 15 in Tables 5 and 6 above were dosed orally to groups of five dogs in a single dose crossover study. Each group was dosed with (1) orally administered uncoated IR tablets containing 90000 IU heparin and 550 mg NaC10 enhancer (batch 7); (2) orally administered uncoated IR tablets containing 90000 IU heparin and 550 mg NaC8 enhancer (batch 3); (3) orally administered uncoated SR tablets containing 90000 IU heparin and 550 mg NaC10 enhancer (batch 15) and (4) s.c. administered heparin solution (5000 IU, control). Blood samples for anti-factor $X_a$ analysis were collected from the jugular vein at various time points. Clinical assessment of all animals pre- and post-treatment indicated no adverse effects on the test subjects. FIG. 8 shows the mean anti-factor $X_a$ response for each treatment, together with the s.c. heparin solution reference. The data in FIG. 8 shows an increase in the plasma anti-factor $X_a$ activity for all of the formulations according to the invention. This result indicates the successful delivery of bioactive heparin using both NaC8 and NaC10 enhancers. Using IR formulations and an equivalent dose of heparin, a larger anti-factor $X_a$ response was observed with the NaC10 enhancer, in spite of the lower dose of NaC10 relative to NaC8 administered (NaC10 dose was half that of NaC8). The anti-factor $X_a$ response can be sustained over longer time profiles relative to IR formulations by the use of SR tablets.

Example 3

Effect of Enhancers on the Systemic Availability of Low Molecular Weight Heparin (LMWH) after Intraduodenal Administration in Rats Male Wistar rats (250 g-350 g) were anaesthetized with a mixture of ketamine hydrochloride (80 mg/kg) and acepromazine maleate (3 mg/kg) given by intra-muscular injection. The animals were also administered with halothane gas as required. A midline incision was made in the abdomen and the duodenum was isolated.

The test solutions, comprising parnaparin sodium (LMWH) (Opocrin SBA, Modena, Italy) with or without enhancer reconstituted in phosphate buffered saline (pH 7.4), were administered (1 ml/kg) via a cannula inserted into the intestine approximately 10-12 cm from the pyloris. The intestine was kept moist with saline during this procedure. Following drug administration, the intestinal segment was carefully replaced into the abdomen and the incision was closed using surgical clips. The parenteral reference solution (0.2 ml) was administered subcutaneously into a fold in the back of the neck.

Blood samples were taken from a tail artery at various intervals and plasma anti-factor $X_a$ activity was determined. FIG. 9 shows the mean anti-factor $X_a$ response over a period of 3 hours following intraduodenal administration to rats of phosphate buffered saline solutions of parnaparin sodium (LMWH) (1000 IU), in the presence of 35 mg of different enhancers [sodium caprylate (C8), sodium nonanoate (C9), sodium caprate (C10), sodium undecanoate (C11), sodium laurate (C12)] and different 50:50 binary mixtures of enhancers, to rats (n=8) in an open loop model. The reference product comprised administering 250 IU parnaparin sodium subcutaneously. The control solution comprised administering a solution containing 1000 IU parnaparin sodium without any enhancer intraduodenally.

FIG. 9 shows that the systemic delivery of LMWH in the absence of enhancer is relatively poor after intraduodenal administration to rats; however, the co-administration of the sodium salts of medium chain fatty acids significantly enhanced the systemic delivery of LMWH from the rat intestine Example 4

Effect of Enhancers on the Systemic Availability of Leuprolide after Intraduodenal Administration in Dogs Beagle dogs (10-15 Kg) were sedated with medetomidine (80 µg/kg) and an endoscope was inserted via the mouth, esophagus and stomach into the duodenum. The test solutions (10 ml), comprising leuprolide acetate (Mallinckrodt Inc, St. Louis, Mo.) with or without enhancer reconstituted in deionized water were administered intraduodenally via the endoscope. Following removal of the endoscope, sedation was reversed using atipamezole (400 µg/kg). The parenteral reference solutions comprising 1 mg Leuprolide reconstituted in 0.5 ml sterile water were administered intravenously and subcutaneously respectively.

Blood samples were taken from the jugular vein at various intervals and plasma leuprolide levels were determined. The resulting mean plasma leuprolide levels are shown in FIG. 10. The results show that, although the systemic delivery of leuprolide when administered intraduodenally without enhancer is negligible, coadministration with enhancer resulted in a considerable enhancer dose dependent enhancement in the systemic delivery of leuprolide; a mean % relative bioavailability of 8% observed for at the upper dose of enhancer.

Example 5

Effect of Enhancers on the Systemic Availability of LMWH after Oral Administration in Dogs (a) Granulate Manufacture A 200 g blend containing parnaparin sodium (47.1%), sodium caprate (26.2%), mannitol (16.7%) and Explotab™ (Roquette Freres, Lestrem, France) (10.0%) was granulated in a Kenwood Chef mixer using water as the granulating solvent. The resulting granulates were tray dried in an oven at 67-68° C. and size reduced through 1.25 mm, 0.8 mm and 0.5 mm screens respectively in an oscillating granulator. The actual potency of the resulting granulate was determined as 101.1% of the label claim.

(b) 30,000 IU LMWH/183 mg Sodium Caprate Instant Release Tablet Manufacture

The granulate described above was bag blended with 0.5% magnesium stearate for 5 minutes. The resulting blend was tableted using 13 mm round concave tooling on a Riva Piccalo tablet press to a target tablet content of 30,000 IU parnaparin sodium and 183 mg sodium caprate. The tablets had a mean tablet hardness of 108 N and a mean tablet weight of 675 mg. The actual LMWH content of the tablets was determined as 95.6% of label claim.

Disintegration testing was carried out on the tablets. One tablet was placed in each of the six tubes of the disintegration basket. The disintegration apparatus was operated at 29-30 cycles per minute using de-ionized water at 37° C. Tablet disintegration was complete in 550 seconds.

(c) 90,000 IU LMWH/0.55 g Sodium Caprate Solution Manufacture 90,000 IU parnaparin sodium and 0.55 g sodium caprate were individually weighed into glass bottles and the resulting powder mixture was reconstituted with 10 ml water.

(d) Dog Biostudy Evaluation 90,000 IU parnaparin sodium and 550 mg sodium caprate was administered as both a solution dosage form (equivalent to 10 ml of the above solution composition) and a fast disintegrating tablet dosage form (equivalent to 3 tablets of the above tablet composition) in a single dose, non randomized, cross-over study in a group of six female beagle dogs (9.5-14.4 Kg) with a seven day washout between treatments. A subcutaneous injection containing 5000 IU parnaparin sodium was used as the reference.

Blood samples were taken from the jugular vein at various intervals and anti-factor $X_a$ activity was determined. Data was adjusted for baseline anti-factor $X_a$ activity. The resulting mean plasma anti-factor $X_a$ levels are summarized in FIG. 11. Both the tablet and solution dosage forms showed good responses when compared with the subcutaneous reference leg. The mean delivery, as determined by plasma antifactor $X_a$ levels, of parnaparin sodium from the solid dosage form was considerably greater than that from the corresponding solution dosage form.

Example 6

Effect of Enhancers on the Systemic Availability of LMWH after Oral Administration in Humans (a) Granulate Manufacture Parnaparin sodium (61.05%), sodium caprate (33.95%) and polyvinyl pyrrolidone (Kollidon 30, BASF AG, Ludwigshafen, Germany) (5.0%) were mixed for 5 minutes in a Gral 10 prior to the addition of water, which was then gradually added, with mixing, using a peristaltic pump until all the material was apparently granulated.

The resultant granulates were tray dried in an oven at either 50° C. for 24 hours. The dried granules were milled through a 30 mesh screen using a Fitzmill M5A (b) 45,000 IU LMWH/275 mg Sodium Caprate Instant Release Tablet Manufacture The parnaparin sodium/sodium caprate/polyvinyl pyrrolidone granulate (78.3%) was blended for 5 minutes with mannitol (16.6%), Explotab (5.0%) and magnesium stearate (1.0%) in a 10 liter V Cone blender. The potency of the resulting blend (480.41 mg/g) was 100.5% of the label claim. The blend was tableted using 13 mm round normal concave tooling on the Piccola 10 station press in automatic mode to a target content of 45,000 IU LMWH and 275 mg sodium caprate. The resulting instant release tablets had a mean tablet weight of 1027 mg, a mean tablet hardness of 108 N and a potency of 97% label claim. The tablets showed a disintegration time of up to 850 seconds and 100% dissolution into pH 1.2 buffer in 30 minutes.

(c) 90,000 IU LMWH/550 mg Sodium Caprate Solution Manufacture

Two instant tablets, each containing 45,000 IU LMWH and 275 mg sodium caprate, were reconstituted in 30 ml water.

(d) Human Biostudy Evaluation 90,000 IU LMWH and 550 mg sodium caprate was orally administered to 12 healthy human volunteers as both a solution dosage form (equivalent to 30 ml of the above solution dosage form) and as a solid dosage form (equivalent to 2 tablets of the above composition) in an open label, three treatment, three period study with a seven day washout between each dose; Treatments A (Instant Release Tablets) and B (Oral Solution) were crossed over in a randomized manner whereas Treatment C (6,400 IU Fluxum™ SC (Hoechst Marion Roussel), a commercially available injectable LMWH product) was administered to the same subjects as a single block.

Blood samples were taken at various intervals and anti-factor $X_a$ activity was determined. The resulting mean anti-factor $X_a$ levels are shown in FIG. 12. Treatments A and B exhibited unexpectedly low responses when compared with the subcutaneous reference treatment. However it should be noted that the mean delivery of LMWH, as measured by plasma anti-factor $X_a$ levels, was considerably higher from the solid dosage form than that from the corresponding solution dosage form for which a mean % bioavailability of only 0.9% was observed.

Example 7

Effect of Enhancers on the Systemic Availability of LMWH after Intrajejunal Administration in Humans (a) Solution Manufacture The following LMWH/sodium caprate combinations were made with 15 ml deionized water:
(i) 20,000 IU LMWH, 0.55 g Sodium Caprate;
(ii) 20,000 IU LMWH, 1.1 g Sodium Caprate;
(iii) 45,000 IU LMWH, 0.55 g Sodium Caprate;
(iv) 45,000 IU LMWH, 1.1 g Sodium Caprate;
(v) 45,000 IU LMWH, 1.65 g Sodium Caprate.

(b) Human Biostudy Evaluation 15 ml of each of the above solutions was administered intrajejunally via a nasojejunal intubation in an open label, six treatment period crossover study in up to 11 healthy human volunteers. 3,200 IU Fluxum™ SC was included in the study as a subcutaneous reference. Blood samples were taken at various intervals and anti-factor $X_a$ activity was determined. The resulting mean anti-factor $X_a$ levels are shown in FIG. 13.

It should be noted that the mean % relative bioavailability for each treatment in the current study was considerably higher than the mean % bioavailability observed for the solution dosage form in Example 6; mean % bioavailabilities ranging from 5% to 9% were observed for the treatments in the current study suggesting that the preferred LMWH oral dosage form containing sodium caprate should be designed to minimize release of drug and enhancer in the stomach and maximize the release of drug and enhancer in the small intestine.

Example 8

Manufacture of Delayed Release Tablet Dosage Form Containing LMWH and Enhancer (a) LMWH/Sodium Caprate Granulate Manufacture A 500 g batch of parnaparin sodium:sodium caprate (0.92:1) was granulated in a Gral 10 using a 50% aqueous solution of Kollidon 30 as the granulating solvent. The resulting granulate was dried for 60 minutes in a Niro Aeromatic Fluidized Bed Drier at a final product temperature of 25° C. The dried granulate was milled through a 30 mesh screen in a Fitzmill M5A. The potency of the resulting dried granulate was determined as 114.8% of the label claim.

(b) 22,500 IU LMWH/275 mg Sodium Caprate Instant Release Tablet Manufacture

The above granulate (77.5%) was added to mannitol (16%), Polyplasdone™ XL (ISP, Wayne, N.J.) (5%) and Aerosil™ (1%) (Degussa, Rheinfelden, Germany) in a 10 IV coned blender and blended for 10 minutes. Magnesium stearate (0.5%) was added to the resulting blend and blending was continued for a further 3 minutes. The resulting blend was tableted on Piccola tablet press using 13 mm round normal concave tooling to a mean tablet weight of 772 mg and a mean tablet hardness of 140 N.

The actual potency of the resulting tablets was determined as 24,017 IU LMWH per tablet.

(c) 22,500 IU LMWH/275 mg Sodium Caprate Delayed Release Tablet Manufacture

The above tablets were coated with a coating solution containing Eudragit L 12.5 (50%), isopropyl alcohol (44.45%), dibutyl sebecate (3%), talc (1.3%), water (1.25%) in a Hi-Coater to a final % weight gain of 5.66%.

The resulting enteric coated tablets remained intact after 1 hour disintegration testing in pH 1.2 solution; complete disintegration was observed in pH 6.2 medium after 32-33 minutes.

Example 9

Manufacture of Instant Release Capsule Dosage Form Containing LMWH and Enhancer (a) 22,500 IU LMWH/275 mg Sodium Caprate Instant Release Capsule Manufacture The granulate from the previous example, part a, was hand filled into Size 00 hard gelatin capsules to a target fill weight equivalent to the granulate content of the tablets in the previous example.

Example 10

Manufacture of Delayed Release Tablet Dosage Form Containing LMWH without Enhancer (a) LMWH Granulate Manufacture A 500 g batch of parnaparin sodium: Avicel™ pH 101 (0.92:1) (FMC, Little Island, Co. Cork, Ireland) was granulated in a Gral 10 using a 50% aqueous solution of Kollidon 30 as the granulating solvent. The resulting granulate was dried for 60 minutes in a Niro Aeromatic Fluidized Bed Drier at an exhaust temperature of 38° C. The dried granulate was milled through a 30 mesh screen in a Fitzmill M5A. The potency of the resulting dried granulate was determined as 106.5% of the label claim.

(b) 22,500 IU LMWH Instant Release Tablet Manufacture

The above granulate (77.5%) was added to mannitol (21%) and Aerosil (1%) in a 25 L V coned blender and blended for 10 minutes. Magnesium stearate (0.5%) was added to the resulting blend and blending was continued for a further 1 minute. The resulting blend was tableted on Piccola tablet press using 13 mm round normal concave tooling to a mean tablet weight of 671 mg and a mean tablet hardness of 144 N.

The actual potency of the resulting tablets was determined as 21,651 IU LMWH per tablet.

(c) 22,500 IU LMWH Delayed Release Tablet Manufacture

The above tablets were coated with a coating solution containing Eudragit L 12.5 (50%), isopropyl alcohol (44.45%), dibutyl sebecate (3%), talc (1.3%) and water (1.25%) in a Hi-Coater to a final % weight gain of 4.26%.

The resulting enteric coated tablets remained intact after 1 hour disintegration testing in pH 1.2 solution; complete disintegration was observed in pH 6.2 medium in 22 minutes.

Example 11

Effect of Controlled Release Dosage Form Containing Enhancer on the Systemic Availability of LMWH after Oral Administration in Dogs (a) Dog Study Evaluation 45,000 IU LMWH was administered to 8 beagle dogs (10.5-13.6 Kg), in an open label, non randomized crossed over block design, as (a) an instant release capsule dosage form containing 550 mg sodium caprate (equivalent to 2 capsules manufactured according to Example 9) (b) a delayed release tablet dosage containing 550 mg sodium caprate (equivalent to two tablets manufactured according to Example 8) and (c) a delayed release tablet dosage not containing any enhancer (equivalent to 2 tablets manufactured according to Example 10). 3,200 IU Fluxum™ SC was included in the study as a subcutaneous reference. Blood samples were taken from the jugular vein at various intervals and anti-factor $X_a$ activity was determined. The resulting mean anti-factor $X_a$ levels are shown in FIG. 14.

It should be noted that in the absence of sodium caprate, the systemic delivery of LMWH was minimal from the delayed release solid dosage form without enhancer. In contrast, a good anti-factor $X_a$ response was observed after administration of the delayed release LMWH solid dosage form containing sodium caprate. The mean anti-factor $X_a$ response from the delayed release dosage form containing sodium caprate was considerably higher than that from the instant release dosage form containing the same level of drug and enhancer.

Example 12

Effect of the Site of Administration on the Systemic Availability of LMWH in Dogs after Co-administration with Enhancer Four beagle dogs (10-15 Kg) were surgically fitted with catheters to the jejunum and colon respectively. The test solutions (10 ml) comprising LMWH with sodium caprate reconstituted in deionized water were administered to the dogs either orally or via the intra-intestinal catheters. 3,200 IU Fluxum™ SC was included in the study as a subcutaneous reference. Blood samples were taken from the brachial vein at various intervals and anti-factor $X_a$ activity was determined. The resulting mean anti-factor $X_a$ levels are shown in FIG. 15. The results show that the intestinal absorption of LMWH in the presence of enhancer is considerably higher than absorption from the stomach.

Example 13

Leuprolide Containing Tablets

Following the same type of approach as used in Examples 1 and 2, leuprolide-containing IR tablets may be prepared according to the formulations detailed in Table 10.

Example 14

Intrajejunal Administration of Alendronate

A study was conducted as an open labeled, randomized, 7 treatment, 6 period study with IJ or PO administrations and at least a 48 hour washout period between each dose. Nineteen (19) healthy male subjects were enrolled into the study and the 15 subjects who were dosed at least once were included in the pharmacokinetic analysis. Pharmacokinetic analysis was based on urinary excretion of alendronate. Table 11 shows the treatments, cumulative amount and % of administered dose excreted in the urine (based on the cumulative amount) in this study.

TABLE 11

MEAN PK PARAMETERS (MEAN ± SD – CV %)

| Treatment | % of Administered Dose excreted In the urine(%) | Cumulative Amount (mg) |
|---|---|---|
| 10 mg Fosamax ™ | 0.61 ± 1.11 | 0.06 ± 0.11 |
| (CV %) | 181.3 | 181.3 |
| 10 mg Alendronate + 0.25 g C10 (IJ) | 3.77 ± 3.16 | 0.38 ± 0.32 |
| (CV %) | 83.9 | 83.9 |
| 10 mg Alendronate + 0.50 g C10 (IJ) | 6.64 ± 4.97 | 0.66 ± 0.50 |
| (CV %) | 74.9 | 74.9 |
| 10 mg Alendronate + 0.75 g C10 (IJ) | 7.66 ± 3.72 | 0.77 ± 0.37 |
| (CV %) | 48.6 | 48.6 |
| 70 mg Alendronate + 0.75 g C10 (IJ) | 10.47 ± 3.63 | 7.33 ± 2.54 |
| (CV %) | 34.7 | 34.7 |

As shown by these data, the gastrointestinal absorption of alendronate was significantly enhanced when administered as an intrajejunal bolus solution with sodium caprate, compared to the current commercially available uncoated instant release Fosamax™ reference tablet.

Example 15

Intrajejunal and Oral Administration of Alendronate

In an open label, partially randomized, 3 treatment, 3 period study with at least a 48 hour washout between each dose, twelve (12) male subjects were dosed at least once during the course of the study and were included in the pharmacokinetic analysis. The following treatments were administered in this study:

TABLE 12

MEAN PK PARAMETERS (MEAN ± SD – CV %)

| PK Parameters | Trt A 17.5 mg Alendronate + 0.5 g C10 (IJ Infusion over 25 min) n12 | Trt B 17.5 mg Alendronate + 1.1 g C10 (IJ Infusion over 25 min) n12 | Trt C 35 mg Fosamax ™ (PO) n12 |
|---|---|---|---|
| Relative Bioavailability (%) | 3376.78 ± 5362.54 | 2664.30 ± 2183.57 | — |
| (CV %) | 158.8 | 82.0 | — |
| Cumulative Amount (mg) | 0.89 ± 0.71 | 1.20 ± 0.74 | 0.21 ± 0.31 |
| (CV %) | 80.0 | 61.5 | 149.4 |
| % of Administered Dose Excreted in the Urine | 5.08 ± 4.07 | 6.88 ± 4.23 | 0.59 ± 0.88 |
| (CV %) | 80.0 | 61.5 | 149.4 |

As shown by these data, the systemic absorption of alendronate was considerably enhanced after co-administration, as an aqueous intrajejunal infusion (over 25 minutes), with sodium caprate. This finding indicates that an enteric coated instant release oral dosage form of alendronate and C10, with enhanced oral absorption of alendronate, as compared to the currently commercially available dosage form, should be advantageous.

Example 16

Oral Administration of Alendronate

A study was conducted to compare the relative bioavailability of alendronate administered as solid oral dosage forms containing an absorption enhancer, with an oral dose of the commercially available reference dosage form Fosamax™. This study was conducted as an open label, partially randomized, single dose, 5 treatment, 5 period study with at least a 48 hour washout between each dose. Sixteen (16) healthy volunteers (13 male and 3 female subjects between 20 and 34 years old and weighing between 64.1 and 81.5 kg) were enrolled and completed all 5 treatments as set forth in Table 13 below.

TABLE 13

| Treatment ID | n | Route | Treatment |
|---|---|---|---|
| Trt A | 16 | PO | 35 mg of Fosamax ™ (Merck Sharp & Dohme Ltd.) administered as 1 tablet with 250 mL tap water Fasted |
| Trt B | 16 | PO | 17.5 mg Alendronate and 0.5 g C10 administered as 2 tablets with 250 mL tap water (8.75 mg Alendronate and 0.25 g C10 per tablet) Fasted HPMC P-55/Opadry coated alendronate/C10 tablets |
| Trt C | 16 | PO | 17.5 mg Alendronate and 0.5 g 010 administered as 2 tablets with 250 mL tap water (8.75 mg Alendronate and 0.25 g C10 per tablet) Fed (High Fat) HPMC P-55/Opadry coated alendronate/C10 tablets |

TABLE 13-continued

| Treatment ID | n | Route | Treatment |
|---|---|---|---|
| Trt D | 16 | PO | 17.5 mg Alendronate and 0.25 g C10 administered as 2 tablets with 250 mL tap water (8.75 mg Alendronate and 0.125 g C10 per tablet) Fasted HPMC P-55 I Opadry coated alendronate/C10 tablets |
| Trt E | 16 | PO | 17.5 mg Alendronate and 0.25 g C10 administered as 1 tablet with 250 mL tap water (17.5 mg Alendronate and 0.25 g C10 per tablet) Fasted HPMC P-55/Opadry coated alendronate/C10 tablets |

Human urine samples were collected across a 36-hour sampling period and analyzed by HPLC with fluorescence detection (assay range: 2 to 2000 ng/mL). The mean % of administered dose excreted in the urine (based on the cumulative amount) for the test treatments, were as follows:

TABLE 14

| Treatment ID | % of Administered Dose Excreted in the Urine (CV %) |
|---|---|
| Trt A | 0.3 ± 0.1 (33.6) |
| Trt B | 1.5 ± 0.6 (40.5) |
| Trt C | 0.2 ± 0.2 (109.8) |
| Trt D | 1.6 ± 1.7 (106.8) |
| Trt E | 1.2 ± 0.9 (79.0) |

Paired t-test analysis was conducted comparing the % Dose Excreted of the test prototypes versus % Dose Excreted for Fosamax™.

TABLE 17

| Treatment | Trt A | Significance | P-Value |
|---|---|---|---|
| Trt B | S | Higher Significance level less than the 0.1% | <0.001 |
| Trt C | S | Lower Significance level 5% | 0.037 |
| Trt D | S | Higher Significance level 1% | 0.006 |
| Trt E | S | Higher Significance level 1% | 0.001 |

S = Statistically significant

A statistically significant increase in the % of the administered dose of alendronate excreted in the urine was observed for the test prototypes administered fasted (dosed as 1 or 2 tablets) compared to that observed for the reference product, Fosamax™. A statistically significant decrease in the percent of the administered dose of alendronate excreted was observed for the test prototype administered fed (Trt C—sig. at 5%) as compared to that observed for Fosamax™. The cumulative amount of administered dose recovered in the urine for the test administrations was 4.6-6.4-fold greater than that observed for Fosamax™.

Increasing the amount of C10 co-administered with alendronate from 0.25 g to 0.5 g did not change the % of administered dose recovered in the urine (1.6±1.7% and 1.5±0.6% respectively). The administration of 17.5 mg alendronate with 0.25 g C10 as 2 tablets (Trt D) resulted in a higher % of administered dose recovered of alendronate (1.6±1.7%) than when administered as 1 tablet according to Trt E (1.2±0.9%).

When 17.5 mg alendronate and 0.5 g C10 was administered as 2 tablets in the fed state (Trt C), 0.2±0.2% of alendronate was determined in the urine. It should be noted that the published literature states that the bioavailability of Fosamax™ is negligible when alendronate is administered with or up to 2 hours after a standard breakfast.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A solid oral dosage form comprising a pharmaceutical composition consisting of:
   (a) a therapeutically effective amount of a bisphosphonate selected from the group consisting of alendronate, clodronate, etidronate, incadronate, ibandronate, minodronate, pamidronate, risedronate, tiludronate and zoledronate;
   (b) a therapeutically effective amount of one or more enhancers, each of which is a salt of a medium chain fatty acid having a carbon chain length of from 8 to 14 carbon atoms and is a solid at room temperature, wherein the one or more enhancers promote absorption of the bisphosphonate at the gastrointestinal tract cell lining; and
   (c) one or more excipients selected from the group consisting of rate-controlling polymeric materials, diluents, lubricants, disintegrants, plasticizers, anti-tack agents, opacifying agents, pigments, and flavorings.

2. The solid oral dosage form of claim 1 wherein the enhancer is a sodium salt of a medium chain fatty acid.

3. The solid oral dosage form of claim 2, wherein the enhancer is selected from the group consisting of sodium caprylate, sodium caprate and sodium laurate.

4. The solid oral dosage form of claim 1, wherein the bisphosphonate is alendronate.

5. The solid oral dosage form of claim 1, wherein the bisphosphonate is clodronate.

6. The solid oral dosage form of claim 1, wherein the bisphosphonate is etidronate.

7. The solid oral dosage form of claim 1, wherein the bisphosphonate is incadronate.

8. The solid oral dosage form of claim 1, wherein the bisphosphonate is ibandronate.

9. The solid oral dosage form of claim 1, wherein the bisphosphonate is minodronate.

10. The solid oral dosage form of claim 1, wherein the bisphosphonate is pamidronate.

11. The solid oral dosage form of claim 1, wherein the bisphosphonate is risedronate.

12. The solid oral dosage form of claim 1, wherein the bisphosphonate is tiludronate.

13. The solid oral dosage form of claim 1, wherein the bisphosphonate is zoledronate.

14. The solid oral dosage form of claim 1, wherein the solid oral dosage form is in the form of a tablet, a capsule or a multiparticulate.

15. The solid oral dosage form of claim 1, wherein the dosage form is a delayed release dosage form.

16. The solid oral dosage form of claim 1, wherein the solid oral dosage form is in the form of a tablet.

17. The solid oral dosage form of claim 8, wherein the tablet is a multilayer tablet.

18. The solid oral dosage form of claim 1, wherein the dosage form comprises a rate-controlling polymer material.

19. The dosage form of claim 18, wherein the rate-controlling polymer material is hydroxypropyl-methylcellulose.

20. The solid oral dosage form of claim 18, wherein the rate-controlling polymer material is a polymer derived from acrylic or methacrylic acid and their respective esters or copolymers derived from acrylic or methacrylic acid and their respective esters.

21. The solid oral dosage form of claim 18, wherein the dosage form is compressed into a tablet form prior to coating with the rate-controlling polymer material.

22. The solid oral dosage form of claim 21, wherein the tablet is a multilayer tablet.

23. The solid oral dosage form of claim 1, wherein the solid oral dosage form is in the form of a multiparticulate.

24. The solid oral dosage form of claim 23, wherein the multiparticulate comprises discrete particles, pellets, minitablets, or combinations thereof.

25. The solid oral dosage form of claim 24, wherein the multiparticulate comprises a blend of two or more populations of particles, pellets, minitablets, or combinations thereof having different in vitro or in vivo release characteristics.

26. The solid oral dosage form of claim 23, wherein the multiparticulate is encapsulated in a hard or soft gelatin capsule.

27. The solid oral dosage form of claim 26, wherein the capsule is coated with the rate-controlling polymer material.

28. The solid oral dosage form of claim 23, wherein the multiparticulate is incorporated into a sachet.

29. The solid oral dosage form of claim 24, wherein the discrete particles, pellets, minitablets, or combinations thereof are compressed into a tablet.

30. The solid oral dosage form of claim 29, wherein the tablet is coated with a rate controlling polymer material.

31. The solid oral dosage form of claim 29, wherein the tablet is a multilayer tablet.

32. The solid oral dosage form of claim 30 wherein the tablet is a multilayer tablet.

33. The solid oral dosage form of claim 1 wherein the bisphosphonate and the enhancer are present in a ratio of from 1:100,000 to 10:1 (drug:enhancer).

34. The solid oral dosage form of claim 33, wherein the ratio is from 1:1,000 to 10:1 (drug:enhancer).

35. The solid oral dosage form of claim 1 comprising about 0.5 µg to about 1,000 mg of drug.

36. The solid oral dosage form of claim 1, wherein the solid oral dosage form is in the form of a delayed release enteric coated tablet.

37. The solid oral dosage form of claim 36, wherein the bisphosphonate and the enhancer are present in a ratio of from 1:1,000 to 10:1 (drug:enhancer).

38. The solid oral dosage form of claim 36, wherein the enhancer is sodium caprate.

39. A process for the manufacture of a solid oral dosage form comprising the steps of:
   a) providing a blend consisting of:
      (i) a bisphosphonate;
      (ii) one or more enhancers to promote absorption of the bisphosphonate at the GIT cell lining, wherein each enhancer is a salt of a medium chain fatty acid having a carbon chain length of from 8 to 14 carbon atoms and is a solid at room temperature; and
      (iii) one or more excipients selected from the group consisting of rate-controlling polymeric materials, diluents, lubricants, disintegrants, plasticizers, anti-tack agents, opacifying agents, pigments, and flavorings; and
   b) forming the solid oral dosage form from the blend by: i) directly compressing the blend; or ii) granulating the blend to form a granulate for incorporation into said solid oral dosage form.

40. The process of claim 38 wherein the drug and the enhancer are blended in a ratio of from 71:100,000 to 10:1 (drug:enhancer).

* * * * *

UNITED STATES PATENT AND TRADEMARK OFFICE
CERTIFICATE OF CORRECTION

| | |
|---|---|
| PATENT NO. | : 8,119,159 B2 |
| APPLICATION NO. | : 11/400689 |
| DATED | : February 21, 2012 |
| INVENTOR(S) | : Cumming et al. |

It is certified that error appears in the above-identified patent and that said Letters Patent is hereby corrected as shown below:

On the Title Page:
Item (63) Related U.S. Application Data: Please delete ", now abandoned"

Item (56) References Cited, Other Publications, Page 3, Left Column, Line 2,
   Declaration;
      Please correct "EP 00905186.3."
         to read -- EP 00905186.3 May 21, 2007. --

Other Publications, Page 3, Left Column, Line 6, Lambent:
      Please correct "(2004)."
         to read -- (2004) December 5, 2006. --

In the Claims:
Column 28, Claim 40, Line 36: Please correct "claim 38" to read -- claim 39 --
   Line 37: Please correct "71:100,000" to read -- 1:100,00 --

Signed and Sealed this
Twenty-ninth Day of May, 2012

David J. Kappos
*Director of the United States Patent and Trademark Office*